United States Patent
Wang et al.

(10) Patent No.: US 7,361,351 B1
(45) Date of Patent: Apr. 22, 2008

(54) METHOD FOR SENSITIZING BOVINE MAMMARY CELLS TO RESPOND TO LPS

(75) Inventors: Yan Wang, Hyattsville, MD (US); Dante S. Zarlenga, Ellicott City, MD (US); Max J. Paape, Silver Spring, MD (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 157 days.

(21) Appl. No.: 11/144,744

(22) Filed: Jun. 6, 2005

Related U.S. Application Data

(62) Division of application No. 10/184,005, filed on Jun. 27, 2002, now Pat. No. 6,984,503.

(51) Int. Cl.
*A61K 39/00* (2006.01)
*G01N 33/53* (2006.01)

(52) U.S. Cl. .................................. 424/185.1; 435/7.1
(58) Field of Classification Search .................. None
See application file for complete search history.

(56) References Cited

U.S. PATENT DOCUMENTS

| 5,543,303 A | 8/1996 | Goyert |
| 5,804,189 A | 9/1998 | Goyert |
| 5,869,055 A | 2/1999 | Juan et al. |

OTHER PUBLICATIONS

Mikayama et al: (PNAS, 1993. 90: 10056-10060.*
Burgess et al (J Cell Biol. 111:2129-2138, 1990.*
Lazar et al. Mol Cell Biol. 8:1247-1252, 1988.*
Wang et al. JBC, 2001 276:49213-49220.*
Haziot, A., et al., "Recombinant Soluble CD14 Inhibits LPS-Induced Tumor Necrosis Factor-α Production by Cells in Whole Blood", *J. of Immunology*, vol. 152, pp. 5868-5876, 1994.
Haziot, A., et al., "Recombinant Soluble CD14 Mediates the Activation of Endothelial Cells by Lipopolysaccharide", *J. of Immunology*, vol. 151, pp. 1500-1507, 1993.
Haziot, A., et al., "Recombinant Soluble CD14 Prevents Mortality in Mice Treated with Endotoxin (Lipopolysaccharide)", *J. of Immunology*, vol. 154, pp. 6529-6532, 1995.
Ikeda, A., et al., "Molecular Cloning of Bovine CD14 gene", *J. Vet. Med. Sci.*, vol. 59, (8), pp. 715-719, 1997.
Majerle, A., et al., "Expression and Refolding of Functional Fragments of the Human Lipopolysaccharide Receptor CD14 in *Escherichia coli* and *Pichia pastoris*", *Protein Expression and Purification*, vol. 17, pp. 96-104, 1999.
Stelter, F., et al., "Different Efficacy of Soluble CD14 Treatment in High-and Low-Dose LPS Models", *European J. of Clinical Investigation*, vol. 28, pp. 205-213, 1998.
Takai, N., et al., "Primary Structure of Rat CD14 and Characteristics of Rat CD14, Cytokine, and NO Synthase mRNA Expression in Mononuclear Phagocyte System Cells in Response to LPS", *J. Of Leukocyte Biology*, vol. 61, pp. 736-744, 1997.
Tapping, R.I., et al., "Cellular Binding of Soluble CD14 Requires Lipopolysaccharide (LPS) and LPS-binging Protein", *Department of Immunology*, Abstract, vol. 272, (37), pp. 23157-23164, Sep. 12, 1997.

* cited by examiner

*Primary Examiner*—Michail Belyavskyi
(74) *Attorney, Agent, or Firm*—John Fado; Evelyn Rabin

(57) ABSTRACT

Studies in mice and humans indicate that membrane CD14 (mCD14) on the cell surface of monocytes, macrophages, and PMN mediates the activation of these cells by LPS. The soluble CD14 (sCD14) present in the circulation also binds to LPS and blocks LPS binding to mCD14. To determine the role of a recombinant bovine soluble CD14 polypeptide in cellular activation by LPS, a recombinant bovine soluble CD14 polypeptide, rbosCD14, was cloned and expressed in a baculovirus expression system. Results indicated that rbosCD14 inhibited the LPS-induced increase in CD18 expression and TNFα mRNA in vitro and reduced mortality in mice injected with LPS. Further, rbosCD14 sensitized mammary epithelial cells to low concentrations of LPS resulting in recruitment of white blood cells and prevention of LPS-induced infection.

1 Claim, 16 Drawing Sheets

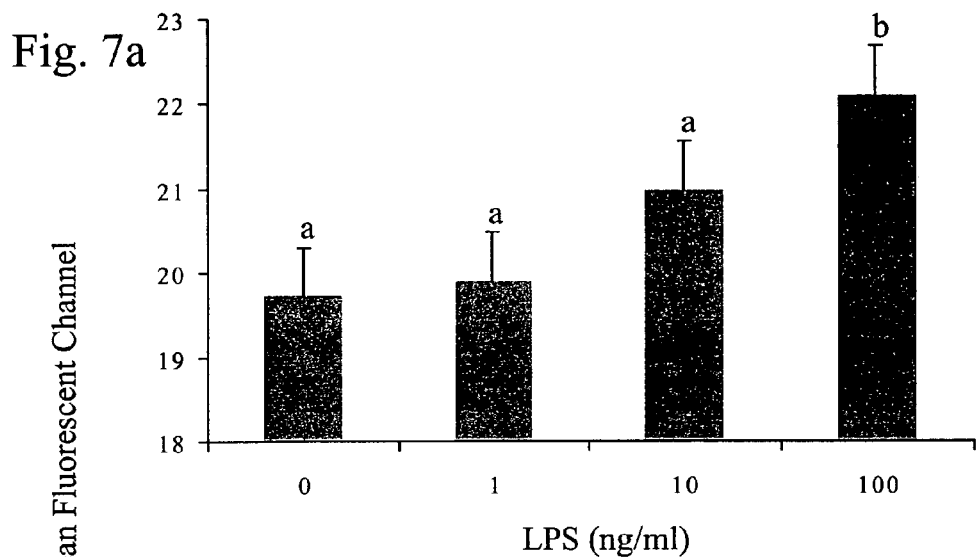
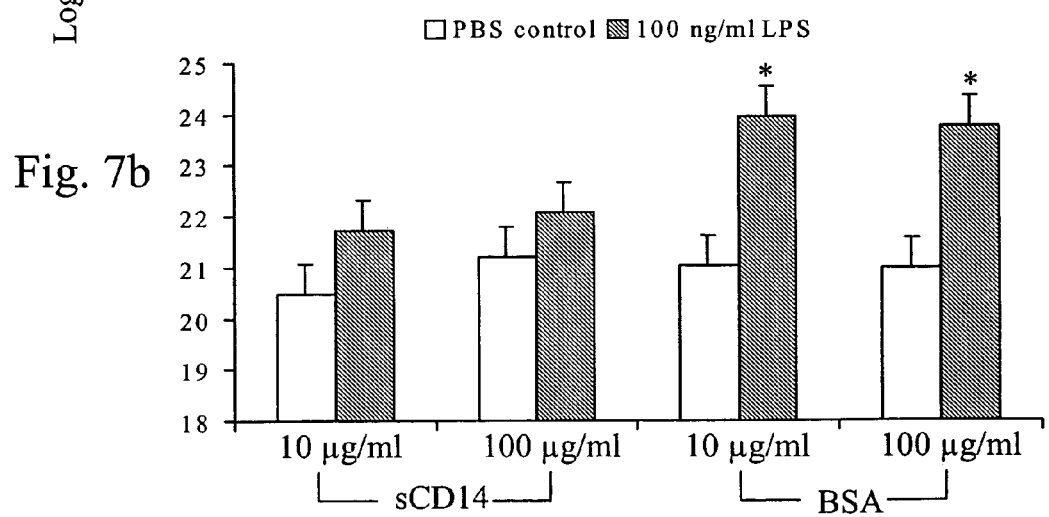

SEQUENCE LISTING

<160> NUMBER OF SEQ ID NOS: 15

<210> SEQ ID NO 1
<211> LENGTH: 1044
<212> TYPE: DNA
<213> ORGANISM: Bos sp.

<400> SEQUENCE: 1

```
aaagaattca tggtgtgcgt gccctacctg ctgctgctgc tgctgccgtc actgctgcgt      60
gtgtctgcgg acacaacaga accctgcaag ctggacgacg acgatttccg ttgtgtctgc     120
aacttcacgg atccgaagcc tgactggtct agcgccgttc agtgtatggt tgccgtcgag     180
gtggagatca gtgccggcgg ccgcagcctg aacagtttct caagggagc cgacaccaac      240
ccgaagcagt atgctgacac aatcaaggct ctgcgcgttc ggcgactcaa gctgggcgct     300
gcacaggttc ctgctcagct tctggtcgcc gttctgcgcg cgctcgggta ctctcgtctc     360
aaggaactga cgcttgagga cctggaggta accggcccaa cgccccgac gcctctggaa      420
gccgctgggc ctgcgctcac caccctcagt ctccgtaacg tatcgtggac aacaggaggt     480
gcctggctcg gcgaactgca gcagtggctc aagcctgggc tcagggtgct gaacattgcc     540
caagcacact cgcttgcctt tccgtgcgca gggctctcca ccttcgaggc gctcaccacc     600
ctagacctgt ctgacaatcc cagtctcggc gacagcgggc tgatggcagc tctctgtccg     660
aacaagttcc cggcccctcc aatatctagcg ctacgcaacg cggggatgga gacgccgagc     720
ggcgtgtgcg cggcgctggc ggcagcgagg gtgcagcccc aaagcctgga cctcagccac     780
aactcgctgc gcgtcaccgc cccgggtgct acccgatgtg tctggcccag tgcactaagg     840
tctctcaatt tgtcgttcgc tgggctggag caagtgccta agggactgcc ccctaagctc     900
agcgtgcttg atctcagctg caacaagcta agcagggagc cacggcgaga cgagctgccc     960
gaggtaaatg acctgactct ggacggaaat ccctttctgg accctggagc cctccagcac    1020
caaaatgacc cgatggtctc ctaa                                            1044
```

<210> SEQ ID NO 2
<211> LENGTH: 344
<212> TYPE: PRT
<213> ORGANISM: Bos sp.

<400> SEQUENCE: 2

```
Met Val Cys Val Pro Tyr Leu Leu Leu Leu Leu Pro Ser Leu Leu
1               5                   10                  15

Arg Val Ser Ala Asp Thr Thr Glu Pro Cys Lys Leu Asp Asp Asp
            20                  25                  30

Phe Arg Cys Val Cys Asn Phe Thr Asp Pro Lys Pro Asp Trp Ser Ser
        35                  40                  45

Ala Val Gln Cys Met Val Ala Val Glu Val Glu Ile Ser Ala Gly Gly
    50                  55                  60

Arg Ser Leu Glu Gln Phe Leu Lys Gly Ala Asp Thr Asn Pro Lys Gln
65                  70                  75                  80

Tyr Ala Asp Thr Ile Lys Ala Leu Arg Val Arg Arg Leu Lys Leu Gly
                85                  90                  95

Ala Ala Gln Val Pro Ala Gln Leu Leu Val Ala Val Leu Arg Ala Leu
            100                 105                 110

Gly Tyr Ser Arg Leu Lys Glu Leu Thr Leu Glu Asp Leu Glu Val Thr
        115                 120                 125
```

```
Gly Pro Thr Pro Pro Thr Pro Leu Glu Ala Ala Gly Pro Ala Leu Thr
        130                 135                 140

Thr Leu Ser Leu Arg Asn Val Ser Trp Thr Thr Gly Gly Ala Trp Leu
145                 150                 155                 160

Gly Glu Leu Gln Gln Trp Leu Lys Pro Gly Leu Arg Val Leu Asn Ile
                165                 170                 175

Ala Gln Ala His Ser Leu Ala Phe Pro Cys Ala Gly Leu Ser Thr Phe
            180                 185                 190

Glu Ala Leu Thr Thr Leu Asp Leu Ser Asp Asn Pro Ser Leu Gly Asp
        195                 200                 205

Ser Gly Leu Met Ala Ala Leu Cys Pro Asn Lys Phe Pro Ala Leu Gln
    210                 215                 220

Tyr Leu Ala Leu Arg Asn Ala Gly Met Glu Thr Pro Ser Gly Val Cys
225                 230                 235                 240

Ala Ala Leu Ala Ala Ala Arg Val Gln Pro Gln Ser Leu Asp Leu Ser
                245                 250                 255

His Asn Ser Leu Arg Val Thr Ala Pro Gly Ala Thr Arg Cys Val Trp
            260                 265                 270

Pro Ser Ala Leu Arg Ser Leu Asn Leu Ser Phe Ala Gly Leu Glu Gln
        275                 280                 285

Val Pro Lys Gly Leu Pro Pro Lys Leu Ser Val Leu Asp Leu Ser Cys
    290                 295                 300

Asn Lys Leu Ser Arg Glu Pro Arg Arg Asp Glu Leu Pro Glu Val Asn
305                 310                 315                 320

Asp Leu Thr Leu Asp Gly Asn Pro Phe Leu Asp Pro Gly Ala Leu Gln
                325                 330                 335

His Gln Asn Asp Pro Met Val Ser
            340

<210> SEQ ID NO 3
<211> LENGTH: 28
<212> TYPE: DNA
<213> ORGANISM: Bos sp.

<400> SEQUENCE: 3
aaagaattca tggtgtgcgt gccctacc                                    28

<210> SEQ ID NO 4
<211> LENGTH: 34
<212> TYPE: DNA
<213> ORGANISM: Bos sp.

<400> SEQUENCE: 4
aaaaagctta cgcgaagcct cgggctcctt gaag                             34

<210> SEQ ID NO 5
<211> LENGTH: 24
<212> TYPE: DNA
<213> ORGANISM: Bos sp.

<400> SEQUENCE: 5
ggagaccatg gggtcatttt ggtg                                        24

<210> SEQ ID NO 6
<211> LENGTH: 18
<212> TYPE: DNA
<213> ORGANISM: Bos sp.
```

```
<400> SEQUENCE: 6
ggggctgctc ctggtgat                                                 18

<210> SEQ ID NO 7
<211> LENGTH: 24
<212> TYPE: DNA
<213> ORGANISM: Bos sp.

<400> SEQUENCE: 7
tttgtggctg gagtggttat taga                                          24

<210> SEQ ID NO 8
<211> LENGTH: 30
<212> TYPE: DNA
<213> ORGANISM: Bos sp.

<400> SEQUENCE: 8
actgtcgaca gaacgagtat gagggaaatc                                    30

<210> SEQ ID NO 9
<211> LENGTH: 29
<212> TYPE: DNA
<213> ORGANISM: Bos sp.

<400> SEQUENCE: 9
gattgtcgac attttctgcc agtgtctcc                                     29

<210> SEQ ID NO 10
<211> LENGTH: 26
<212> TYPE: DNA
<213> ORGANISM: Bos sp.

<400> SEQUENCE: 10
ggagatgatc tctcaacttt aactgg                                        26

<210> SEQ ID NO 11
<211> LENGTH: 25
<212> TYPE: DNA
<213> ORGANISM: Bos sp.

<400> SEQUENCE: 11
cattatagtc aagggcatat cccac                                         25

<210> SEQ ID NO 12
<211> LENGTH: 36
<212> TYPE: DNA
<213> ORGANISM: Bos sp.

<400> SEQUENCE: 12
caagaattca ggtcctcttc tcaagcctca agtaac                             36

<210> SEQ ID NO 13
<211> LENGTH: 34
<212> TYPE: DNA
<213> ORGANISM: Bos sp.

<400> SEQUENCE: 13
tttggatccc ggcaggttga tctcagcact gagg                               34

<210> SEQ ID NO 14
<211> LENGTH: 29
<212> TYPE: DNA
<213> ORGANISM: Bos sp.
```

```
<400> SEQUENCE: 14
gaattcatga cttccaaact ggctgttgc                                              29

<210> SEQ ID NO 15
<211> LENGTH: 23
<212> TYPE: DNA
<213> ORGANISM: Bos sp.

<400> SEQUENCE: 15
tcatggatct tgcttctcag ctc                                                    23
```

METHOD FOR SENSITIZING BOVINE MAMMARY CELLS TO RESPOND TO LPS

This application is a divisional application of application Ser. No. 10/184,005, filed Jun. 27, 2002, now pending, which is herein incorporated by reference in its entirety.

BACKGROUND OF THE INVENTION

1. Field of the Invention

In humans and mice, the membrane bound form of CD14 (mCD14) found on the cell surface of monocytes, macrophages and polymorphonuclear neutrophils (PMN) mediates the activation of these cells by lipopolysaccharide (LPS). Soluble CD14 (sCD14), present in the circulation, binds to LPS and blocks its binding to mCD14. In addition, sCD14, present in milk, is involved in sensitization of mammary duct epithelial cells and induction of an immune response. This invention relates to the cloning and expression of a form of recombinant bovine soluble CD14, identified here as rbosCD14, and its functional roles.

2. Description of the Relevant Art

Bovine coliform mastitis is an inflammation of the mammary gland caused by Gram-negative bacteria, where *Escherichia coli* is the most common pathogen. Mastitis is the most costly disease in the dairy industry, with economic losses of approximately two billion dollars annually in the United States. Mastitis results in decreased milk production, increased veterinary costs, and early culling or death of animals. Coliform mastitis is the most prevalent form of clinical mastitis, with infection by *E. coli* being the most frequent. About 80% of all intramammary infections by coliform bacteria will result in clinical mastitis, and 10% will result in peracute mastitis with a sudden onset of septic shock. Because coliforms are present in the cow's environment, they cannot be eradicated on a practical basis. Conventional herd management practices such as pre- and post-milking teat dipping and dry cow antibiotic therapy are unable to reduce the incidence of new infections. Coliform mastitis will exist as an animal health problem even in well managed herds. Conventional antibiotic treatment, extensive fluid supplementation, and metabolic support are not effective in relieving disease symptoms (1996. *Current Concepts of Bovine Mastitis*. National Mastitis Council, Madison, Wis.). Therefore, it is important to develop novel therapeutic regimens to control symptoms associated with acute coliform mastitis. Understanding the pathophysiological response of the mammary gland to coliform infections is critical in order to design such novel preventive and therapeutic regimens for clinical coliform mastitis.

It has been postulated that microbial products, often present in adjuvants, act on the innate immune system to elicit signals for activation of the adaptive immune system (Janeway, C. A. Jr. 1989. *CSHSQB* 54 (Pt 1): 1-13; Medzhitov et al. 1997. *Curr. Opin. Immunol.* 9: 4-9). Kinetic studies of experimental coliform mastitis induced by the intramammary injection of *E. coli* showed that inflammatory response will not be initiated until bacterial growth reaches a certain level (Shuster et al. 1995. *Proc. Soc. Exp. Biol. Med.* 210: 140-149; Shuster et al. 1996. *Am J. Vet. Res.* 57: 1569-1575). Uncontrolled bacterial growth results in a buildup in the concentration of microbial products that can be recognized by the host as a danger signal for the presence of a bacterial infection. It is conceivable that this signal is comprised of a conserved group of molecules across bacterial groups, and the host processes a sensitive machinery to detect this danger signal after it exceeds a certain threshold. Lipopolysaccharide (LPS) is one of the best characterized candidates of a danger signal because LPS is a component of the outer membrane of all Gram-negative bacteria and is released by actively growing, damaged, and dead bacteria (Petsch et al. 2000. *J. Biotechnol.* 76: 97-119). The toxicity of LPS is attributed to lipid A, a conserved domain of LPS.

CD14 is a receptor that binds to LPS and mediates the LPS-induced activation of host cells (Wright et al., supra). Two forms of CD14 exist. Membrane bound CD14 (mCD14) is present on the cell surface of monocytes, macrophages, and PMN, and mediates activation of those phagocytes by low concentrations of LPS in the presence of LPS-binding protein (LBP). Soluble CD14 (sCD14) is present in serum/plasma and urine of nephritic patients (Maliszewski et al. 1985. *J. Immunol.* 135: 1929-1936; Bazil et al. 1986. *Eur. J. Immunol.* 16: 1583-1589; Haziot et al. 1988. *J. Immunol.* 141: 547-552), and mediates activation of cells not bearing mCD14, including epithelial cells and endothelial cells (Arditi et al. 1993. *Infect. Immun.* 61: 3149-3156; Frey et al. 1992. *J. Exp. Med.* 176: 1665-1671; Pugin et al. 1993. *Proc. Natl. Acad. Sci. USA* 90: 2744-2748; Read et al. 1993. *Proc. Nat. Acad. Sci. USA* 90: 9887-9891). Macrophages are the predominant cell type in milk from uninfected bovine mammary glands. Bovine macrophages and PMN in milk express mCD14 on their cell surface (Paape et al. 1996. *Am. J. Vet. Res.* 57: 477-482). Labeta et al. (2000. *J. Exp. Med.* 191: 1807-1812) have reported the detection of sCD14 in human milk. Because bovine mammary epithelial cells do not express mCD14 as determined by PCR (data not shown), we have postulated that shedding of mCD14 from cell surfaces of milk macrophages and PMN is probably the major source of sCD14 in bovine milk. We too have detected sCD14 in human milk using anti-human CD14 mAb 60bca by Western blot; however, the concentration of sCD14 in bovine milk has not been heretofore determined due to the lack of a reliable ELISA for measuring bovine sCD14.

Binding of LPS to mCD14 on the surface of mCD14-bearing cells in the presence of LPS binding protein initiates the production of pro-inflammatory cytokines and mediators that are necessary for the host defense against infection by Gram-negative bacteria (Kurland et al. 1978. *J. Exp. Med.* 147: 952-957; Dentener et al., supra). For example, binding leads to an increase in the adhesion of PMN to a fibrinogen-coated surface (Wright, supra), translocation of nuclear factor κβ (NF-κβ, Morrison et al. 1979. *Adv. Immunol.* 28: 293-450), and the release of tumor necrosis factor-α (TNF-α) by monocytes and macrophages (Dentener, supra), all indicators of activation. However, overwhelming release of cytokines and pro-inflammatory mediators can be detrimental to the host (Bass et al. 1998. In: *Phagocyte Function: A Guide for Research and Clinical Evaluation*, J. P. Robinson and G. F. Babcock, Eds. Wiley-Liss, New York, pages 97-123). In severe conditions such as endotoxemia or septic shock, systemic responses induced by LPS can result in fever, hypertension, and organ injury (Bone, R. C. 1991. *Chest* 100: 802-808). Due to the lack of an effective treatment, mortality associated with Gram-negative septic shock in hospitals remains high at 25-30% (Glauser et al. 1991. *Lancet* 338: 732-739). The addition of sCD14 inhibits these activation effects of LPS on leukocytes in vitro by binding LPS and preventing its interaction with mCD14 (Maliszewski, C. R. 1991. *Science* 252: 1321-1322; Haziot et al. 1994. *J. Immunol.* 152: 5868-5876; Juan et al. 1995. *J. Biol. Chem.* 270: 1382-1387). The inhibitory effect of human sCD14 on LPS-induced activation of leukocytes protects mice from a lethal challenge of LPS (Haziot et al. 1995.

*Prog. Clin. Biol. Res.* 392: 349-351). Therefore, sCD14 may be a potential therapeutic tool in controlling the acute inflammatory response caused by Gram-negative bacterial infections such as is seen in bovine coliform mastitis.

In addition, mammals process a CD14-dependent pathway to detect subpicomolar concentrations of LPS that activate host cells to mount an inflammatory response for clearance of bacteria (Dentener et al. 1993. *J. Immunol.* 150: 2885-2891; Ulevitchand et al. 1999. *Curr. Opin. Immunol.* 11: 19-22; Wright et al. 1990. *Science* 249: 1431-1433). Studies using $LBP^{-/-}$ deficient mice have shown that defects in CD14-dependent cellular responses to LPS protected mice from a lethal challenge with LPS, but prevented bacterial clearance after bacterial challenge in vivo (Jack et al. 1997. *Nature* 389: 742-745; Wurfel et al. 1997. *J. Exp. Med.* 186: 2051-2056). A delay in leukocyte recruitment after intramammary coliform infections leads to approximately 10 times more bacteria (Erskine et al. 1989. *Am. J. Vet. Res.* 50: 2093 2100). These studies emphasize the importance of a rapid and early inflammatory reaction in protecting the host from an overwhelming bacterial infection.

Previous studies have shown that human sCD14 forms a complex with LPS and mediates activation of cells not bearing mCD14 in the presence of low concentrations of LPS (Pugin et al., Frey et al., supra). Therefore, bovine soluble CD14-induced activation may contribute to udder swelling and changes in vascular and mammary epithelium permeability, which are the first two clinical signs observed after experimental coliform infections (Shuster et al. 1995, 1996, supra). Experiments to determine correlations among mammary gland sensitivity to LPS, milk somatic cell counts (MSCC), and the incidence of coliform mastitis after experimental exposure to *E. coli* facilitate the understanding of the initiation of inflammatory response in the bovine mammary gland making possible the designing of regimens for controlling coliform mastitis.

The production of a form of recombinant bovine soluble CD14, i.e., rbosCD14, by a baculovirus and insect cell expression system provides both a useful research tool for studying cattle immune responses to LPS and a potential therapeutic regimen for bovine diseases caused by Gram-negative bacteria, such as is the case with peracute coliform mastitis. As a bovine therapeutic, there is a role for a recombinant sCD14 molecule both as an inhibitor of the activation which occurs in an acute inflammatory response and as a sensitizer of bovine mammary ductal epithelial cells, thereby serving as an early signal for recruitment of leukocytes and activation of an immune response.

SUMMARY OF THE INVENTION

We have discovered a recombinant nucleic acid molecule that encodes for a bovine soluble CD14. The DNA sequence may be inserted into DNA molecules such as cloning vectors or expression vectors for the transformation of cells and the production of a rbosCD14.

In accordance with this discovery, it is an object of the invention to provide novel recombinant nucleic acid molecules which encode a soluble form of bovine CD14.

It is also an object of the invention to provide the novel peptides or proteins encoded by said nucleic acid molecules.

It is an added object of the invention to provide recombinant molecules containing the DNA sequences encoding the above polypeptides, vectors, hosts transfected with such DNA sequences and molecules, and methods of making the polypeptides recombinantly, synthetically or semi-synthetically.

Further, the invention can comprise fusion proteins comprising one of the peptides described above comprising one or more epitopes of a recombinant bovine soluble CD14 polypeptide. In addition, the invention can comprise fusion proteins comprising an unrelated peptide expressed by a regulatory DNA segment operably linked to a DNA nucleotide sequence encoding a fusion protein comprising one of the peptides described above. It is part of this invention to provide the genes which encode these fusion proteins. Still part of this invention are fusion RNA and DNA polymers comprising the RNA or DNA of this invention and a second unrelated polyRNA or polyDNA segment.

It is yet an additional object of the invention to provide the novel nucleotides encoding the proteins described herein or a portion of the nucleotide sequences for use as primers and probes for PCR assays.

Another object of the invention relates to a method of inhibiting or ameliorating mastitis in an individual comprising administering to an individual in need of such treatment an amount of a recombinant bovine soluble CD14 polypeptide effective to prevent or decrease the severity of bovine mastitis.

Still another object of the invention relates to a method of sensitizing an individual to activate an immune response to low concentrations of LPS comprising administering to an individual an amount of a recombinant bovine soluble CD14 polypeptide effective to sensitize cells not expressing mCD14 on their surfaces.

An added object of the invention is to provide compositions useful for inhibiting or ameliorating mastitis in an individual.

The polypeptides of this invention are useful treat pathologies dependent on the formation of a LPS/bovine sCD14 complex.

The polypeptides of this invention and the DNA sequences encoding them may also be used to prepare recombinant or synthetic fusion proteins, which comprise a functional LPS-binding domain of a rbosCD14 polypeptide, as defined above, and another domain of a protein or polypeptide other than the rbosCD14 of the invention. The LPS-binding domain portion of the fusion proteins allows the other polypeptides to be targeted specifically to LPS binding cells. DNA sequences encoding these fusion proteins are also part of this invention.

One example of such fusion proteins of this invention is novel fusion proteins containing a portion of rbosCD14 containing a functional LPS-binding domain, as defined above, fused to at least a portion of the Fc region of an immunoglobulin (Ig).

In addition to the monomeric form of the LPS-binding polypeptides and fusion proteins of this invention, multimeric forms comprised of rbosCD14 sequences are also enabled by this invention. Such forms may have enhanced affinity for LPS, enhanced immunogenicity and/or enhanced ability to inhibit or enhance activation, through more effective or multiplied formation of LPS/rbosCD14 complexes. Also, such multimeric forms may be more effective in competitive binding of LPS, making them more useful as inhibitors or sensitizers.

In addition, this invention contemplates antibodies recognizing the polypeptides and fusion proteins of this invention. Polyclonal and monoclonal antibodies to the polypeptides and fusion proteins of this invention may be obtained by immunizing an animal with polypeptides or fusion proteins of this invention.

Also part of this invention is a diagnostic kit for identifying bovine CD14 genes, comprising PCR primers and probes; and instructions for the use of the kit.

Other objects and advantages of the invention will become readily apparent from the following description.

BRIEF DESCRIPTION OF THE DRAWINGS

FIGS. 7A and 7B illustrate the effect of rbosCD14 on expression of CD18 on the cell surface of PMN in whole blood stimulated with LPS (100 ng/ml). FIG. 7A: Whole blood (100 µl) was incubated with LPS at 37° C. in 5% $CO_2$ for 90 min; FIG. 7B: BSA or rbosCD14 was incubated with PBS (□) or LPS (■) at 37° C. in 5% $CO_2$ for 60 min, and incubated with whole blood at 37° C. in 5% $CO_2$ for 90 min. The binding of anti-bovine CD18 mAb to PMN was determined by flow cytometry. The log mean fluorescence channel was used as a measure of mAb binding. The data from three experiments performed in duplicate are expressed as means and standard errors. * denotes that means within the same concentration of rbosCD14 or BSA differ (P<0.05).

DETAILED DESCRIPTION OF THE INVENTION

Figure 1:
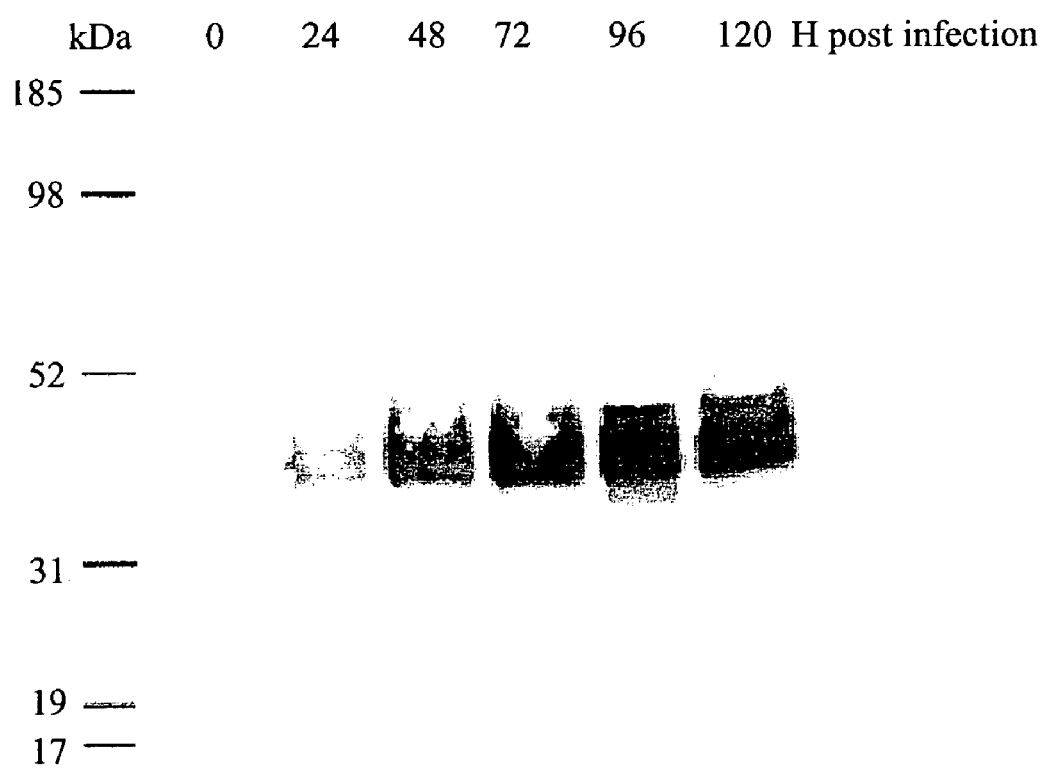
FIG. 1 shows the expression of a C-terminal truncated recombinant bovine soluble CD14 polypeptide, i.e., the rbosCD14 of the invention, in culture supernatant of infected sf-9 cells at various time points post infection (pi). Proteins in the culture supernatant (20 µl) for each time point were separated on a 4-12% NuPAGE (Novex) gel under reducing conditions, and were transferred to nitrocellulose membrane. The membrane was probed with anti-tetra-HIS monoclonal antibody (mAb).

The present invention provides a recombinant bovine soluble CD14 polypeptide, rbosCD14. It further provides therapeutic uses of rbosCD14 both as an inhibitor of the activation which occurs in an acute inflammatory response and as a sensitizer of bovine mammary ductal epithelial cells resulting in leukocyte recruitment and initiation of an immune response.

The present invention provides an isolated recombinant bovine soluble CD14 polypeptide, rbosCD14 (SEQ ID NO:2), and the nucleic acid sequences that encode rbosCD14 polypeptide (SEQ ID NO:1).

It will be appreciated by those of skill in the art that, due to the degeneracy of the genetic code, DNA molecules comprising many other nucleotide sequences will also be capable of encoding the polypeptides of this invention. It is understood that all such equivalent sequences are operable variants of the disclosed sequence, since all give rise to the same protein (i.e., the same amino acid sequence) during in vivo transcription and translation, and are hence encompassed by the instant invention.

A "variant" of rbosCD14 may have an amino acid sequence that is different by one or more amino acid "substitutions". The variant may have "conservative substitutions", wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions, or both. Guidance in determining which and how many amino acid residues may be substituted, inserted or deleted without abolishing biological or immunological activity may be found using computer programs well known in the art, for example, DNASTAR software. The term "biological activity" refers to rbosCD14 having structural, regulatory or biochemical functions of a naturally occurring bovine sCD14. Likewise, "immunological activity" defines the capability of a natural, recombinant or synthetic bovine sCD14, or any oligopeptide thereof, to induce a specific immune response in appropriate animals or cells and to bind with specific antibodies.

The phrase "conservative substitution" also includes the use of a chemically derivatized residue in place of a non-derivatized residue. "Chemical derivative" refers to the chemical modification of a nucleic acid sequence encoding rbosCD14 or the encoded rbosCD14 wherein the subject nucleic acid or polypeptide has one or more residues chemically derivatized by reaction of a functional side group. Examples of such modifications would be replacement of hydrogen by an alkyl, acyl, or amino group; however, replacements are not limited to these groups. A nucleic acid derivative would encode a polypeptide which retains essential biological characteristics of natural bovine sCD14. Also included are those peptides which contain one or more naturally-occurring amino acid derivatives of the twenty standard amino acids, e.g., 5-hydroxylysine or ornithine may be substituted for lysine. Other modifications include hydroxylation of proline, phosphorylation of hydroxyl groups of seryl or threonyl residues, oxidation of the sulfur atom in Cys, methylation of the alpha-amino groups of lysine, arginine, and histidine side chains (T. E. Creighton, Proteins: Structure and Molecule Properties, W. H. Freeman & Co., San Francisco, pp. 79-86 (1983)), acetylation of the N-terminal amine, and, in some instances, amidation of the C-terminal carboxyl groups.

The term "peptide" as used herein refers to a molecular chain of amino acids with a biological activity (e.g., capable of binding LPS), and does not refer to a specific length of the product. Thus, inter alia, proteins, oligopeptides, polypeptides and fusion proteins as well as fusion peptides are included.

Such derivatized moieties may improve the solubility, absorption, biological half life, and the like. The moieties may alternatively eliminate or attenuate any undesirable side effect of the protein and the like. Moieties capable of mediating such effects are disclosed, for example, in *Remington's Pharmaceutical Sciences*, 16th ed., Mack Publishing Co., Easton, Pa. (1980). Modifications of such polypeptide properties as redox or thermal stability, hydrophobicity, susceptibility to proteolytic degradation or the tendency to aggregate with carriers or into multimers are assayed by methods well known to the ordinarily skilled artisan.

The polypeptides of the invention may also be covalently or noncovalently associated with a carrier molecule, such as a polypeptide or non-CD14 protein, a linear polymer (such as polyethylene glycol, polylysine, etc), a branched-chain polymer (see, for example, U.S. Pat. No. 4,289,872 to Denkenwalter et al., issued Sep. 15, 1981; U.S. Pat. No. 5,229,490 to Tam, issued Jul. 20, 1993; WO 93/21259 by Frechet et al., published 28 October, 1993); a lipid; a cholesterol group (such as a steroid; or a carbohydrate or oligosaccharide.

The present invention also relates to recombinant DNA molecules comprising the aforementioned DNA sequences. The DNA sequences of the invention can be used to prepare recombinant DNA molecules by cloning in any suitable vector. A variety of vector-host combinations may be employed in practicing the present invention.

The recombinant DNA molecules of this invention are capable of directing expression of the rbosCD14 polypeptides of this invention in hosts transformed therewith. A DNA sequence encoding rbosCD14 polypeptides of this invention must be operatively linked to an expression control sequence for such expression. The term "operatively linked" as used herein refers to positioning in a vector such that transcription and translation of the coding sequence is directed by the control sequence.

To construct a recombinant DNA molecule capable of directing expression of the rbosCD14 polypeptides of this invention, the DNA sequences encoding these polypeptides may be inserted into and expressed using a wide variety of vectors. Vectors used in practicing the present invention are selected to be operable as cloning vectors or expression vectors in the selected host cell. Numerous vectors are known to those of skill in the art, and selection of an appropriate vector and host cell is a matter of choice. The vectors may, for example, be bacteriophage, plasmids, viruses, or hybrids thereof. A number of prokaryotic expression vectors are described in U.S. Pat. Nos. 4,652,525, 4,440,859, 4,436,815, and 4,342,832, and a number of eukaryotic expression vectors have also been described in U.S. Pat. Nos. 4,546,082, 4,510,245, and 4,446,235.

Further, the vectors may be non-fusion vectors (i.e., those producing the protein of the invention not fused to any heterologous polypeptide), or alternatively, fusion vector (i.e., those producing the protein fused to a vector encoded polypeptide). The fusion proteins would of course vary with the particular vector chosen. Suitable non-fusion plasmid vectors for use with *E. coli* include but are not limited to pTrc99 for use with *E. coli* JM 105, or pANK-12, pANH-1 or pPL2 for use with *E. coli* MZ 1. Conversely, suitable fusion plasmid vectors include pGEX and pMC1871 for use with *E. coli* JM 105, PMAL with *E. coli* PR 722, pVB2 with *E. coli* LA5709, pTrcHis with *E. coli* INV F' and DH5, $pCO_5$ with *E. coli* $N_{64}O_5$, and pRIT2T or pEZZ 18 with *E. coli* N4830-1. Other, non-*E. coli* expression systems which may also be employed include pAc360 or pBluescript for use with SP2 or High 5 insect cells, pYesHis with the yeast *C. cerevisiae* INVSc1 or INVSc2, pLS405 with *Salmonella dublin* SL598, and pYUB12 with *Mycobacterium smegmatis* or *M. bovis*. Still other suitable vector-host combinations that may be used in practicing the instant invention are described, for example, in U.S. Pat. No. 5,122,471, the contents of which are incorporated by reference herein.

Furthermore, within each specific expression vector, various sites may be selected for insertion of these DNA sequences. These sites are usually designated by the restriction endonuclease which cuts them. They are well recognized by those of skill in the art. It will be appreciated, however, that an expression vector useful in this invention need not have a restriction endonuclease site for insertion of the chosen DNA fragment. Instead, the vector may be joined to the fragment by alternative means.

The DNA sequences of the invention may be inserted into the desired vector by known techniques. If, however, the vector is to serve as an expression vector, the vector should have a promoter, and the DNA sequence should be inserted in the vector downstream of the promoter and operationally associated therewith. While control sequences may be ligated to the coding sequence prior to insertion into the vector, preferably, the vector should be selected so as to have a promoter operable in the host cell into which the vector is to be inserted (that is, the promoter should be recognized by the RNA polymerase of the host cell). In addition, the vector should have a region which codes for a ribosome binding site positioned between the promoter and the site at which the DNA sequence is inserted so as to be operatively associated with the DNA sequence of the invention once inserted (in correct translational reading frame therewith). The vector should be selected to provide a region which codes for a ribosomal binding site recognized by the ribosomes of the host cell into which the vector is to be.

The expression vector, and in particular the site chosen for insertion of a selected DNA fragment and operative linking to an expression control sequence, is determined by a variety of factors. These factors include, e.g., the number of sites susceptible to a particular restriction enzyme, the size of the polypeptide to be expressed, susceptibility of the desired polypeptide to proteolytic degradation by host cell enzymes, contamination or binding of the polypeptide to be expressed by host cell proteins difficult to remove during purification, expression characteristics, such as the location of start and stop codons relative to the vector sequences, and other factors recognized by those skilled in the art. The choice of a vector and an insertion site for a DNA sequence is determined by a balance of these factors and not all selections will be equally effective for a given case.

Useful expression vectors for eukaryotic hosts include, for example, vectors comprising expression control sequences from SV40, bovine papilloma virus, adenovirus and cytomegalovirus, and vectors useful specifically in insect cells, such as pVL 941. Useful bacterial expression vectors include known bacterial plasmids, e.g., plasmids from *E. coli* including colE1, pcRl, pBR322, pMB9 and their derivatives; wider host range plasmids, such as RP4; the numerous derivatives of phage lambda, e.g., NM 989 and the lambda gt series; other DNA phages, e.g., M13 and other filamentous single-stranded DNA phages; and commercially available high expression vectors, e.g., the pGEM series and the lambda Zap vectors. Useful mammalian cell expression vectors include, for example, PNUT. Vectors useful in yeasts include, for example, the 2μ plasmid and derivatives thereof.

Such expression vectors are also characterized by at least one expression control sequence that may be operatively linked to the DNA sequences of this invention inserted in the vector in order to control and to regulate the expression of that cloned DNA sequence. Examples of useful expression control sequences include the malE system, the OmpA system, the lac system, the trp system, the tac system, the trc system, major operator and promoter regions of phage lambda, the control region of fd coat protein, the glycolytic promoters of yeast, e.g., the yeast acid phosphatase, e.g., Pho5, the promoters of the yeast mating factors, and promoters derived from polyoma, adenovirus, retrovirus, and simian virus, e.g., the early and late promoters of SV40, eukaryotic cell promoters, such as the metallothionein promoter and other sequences known to control the expression of genes of prokaryotic or eukaryotic cells and their viruses or combinations thereof.

The recombinant DNA molecules of the present invention may also comprise other DNA coding sequences fused to and in frame with the DNA sequences of this invention. For example, such constructs may be characterized by an ATG start codon fused directly to the nucleotides encoding the first amino acid of the rbosCD14 polypeptide. This construction may produce an f-Met polypeptide. However, it will be understood that the initial methionine may be cleaved during expression in a transformed host or may be subsequently removed. Alternatively, a DNA sequence encoding a bacterial or eukaryotic signal sequence may be fused to the 5' end of a DNA sequence encoding a rbosCD14 polypeptide of this invention. This would allow the expressed product to be either secreted or targeted to a specific subcellular compartment within the host cell. Most signal sequences are removed by the host cell after performing their targeting function, thus obviating the need for removal after purification of the desired polypeptide. Many signal sequences, as well as the DNA sequences encoding them, are known in the art. The fusion protein of such signal sequence DNA to and in frame with the sequence encoding a rbosCD14 polypeptide of this invention can be achieved by standard molecular biology techniques.

Alternatively, a DNA sequence encoding a rbosCD14 polypeptide of this invention may be expressed as a fusion protein by in-frame ligation to a second DNA sequence encoding a host cell polypeptide. The expression of a fusion protein may afford several advantages, such as increased resistance to host cell degradation, ease of identification based upon the activity or antigenicity of the host cell polypeptide, and ease of purification, based upon the physical or immunological properties of the host cell polypeptide.

DNA sequences encoding fusion proteins that have an amino-terminal region characterized by the amino acid sequence of a rbosCD14 of the invention and a carboxy-terminal region comprising a domain of a protein or polypeptide other than rbosCD14 are also encompassed by the invention. Such domains include, for example, the Fc region of an immunoglobulin. In the fusion proteins of this invention, the LPS-binding polypeptides of this invention are fused to at least a portion of the Fc region of an immunoglobulin. In these fusion proteins, the LPS-binding polypeptides form the amino-terminal portion, and the Fc region forms the carboxy terminal portion.

This invention encompasses a hybrid vector, that comprises a vector capable of replication, transcription and expression of DNA segments operably linked thereto; and a DNA segment encoding a polypeptide of this invention comprising the peptide disclosed herein operatively linked thereto, wherein when the vector is placed in an appropriate host it can express the polypeptide encoded by the DNA segment. Examples of such vectors are pGex (Pharmacia), baculovirus, pET-9d (Novagen) or pRSET T7 (Invitrogen). However, other vectors may also be utilized. The vector may be a eukaryotic or a prokaryotic vector depending on the host selected for transfection and in which the gene product is going to be expressed. Still part of this invention is another hybrid vector, that comprises a vector capable of replication, transcription and expression of DNA segments operably linked thereto; and a DNA segment comprising a DNA fragment encoding at least one of the polypeptides of the invention and a second unrelated DNA segment, both sequences being operably linked to one another and to the vector. The preparation of the hybrid vector described above is known in the art and need not be further described herein (Smith, D., and Johnson, K., "Single Step Purification of Polypeptides Expressed in *E. coli* as Fusions with Glutathione S-transferase", Gene 67:31 (1988); Studier, F. W., Rosenberg, A. H., Dunn, J. J., and Dubendorff, J. W., "Use of T7 RNA Polymerase to Direct Expression of Cloned Genes", Meth. Enzymol. 185:60-89 (1990)).

This invention also relates to hosts transformed with the recombinant DNA molecules described above. Useful hosts which may be transformed with these recombinant DNA molecules and which may be employed to express the rbosCD14 polypeptides of this invention may include well known eukaryotic and prokaryotic hosts, such as strains of *E. coli, Pseudomonas, Bacillus, Streptomyces, Saccharomyces*, animal cells, such as COS cells, Chinese hamster ovary (CHO) cells, BHK cells, human tissue cells, insect cells e.g., *Spodoptera frugiperda* (Sf9 or Sf21) or *Trichoplusia ni* (high five), and plant cells in tissue culture. However, other hosts may also be utilized. The preferred host cells for polypeptides claimed herein are sf9 cells or "high five" cells.

It will be appreciated that not all host/expression vector combinations will function with equal efficiency in expressing DNA sequences encoding the rbosCD14 polypeptides of this invention. However, a particular selection of a host-expression vector combination may be made by those of skill in the art after due consideration of the principles set forth herein without departing from the scope of this invention. For example, the selection should be based on a balancing of a number of factors. These factors include, for example, compatibility of the host and vector, toxicity of the polypeptides encoded by the DNA sequence to the host, vector copy number and the ability to control that copy number, the expression of other proteins encoded by the vector, such as antibiotic markers, ease of recovery of the desired protein, expression characteristics of the DNA sequences and the expression control sequences operatively linked to them, biosafety, costs and the folding, form or any other necessary post-expression modifications of the desired polypeptide.

The transformed host is cultured under conventional fermentation conditions so that the desired peptides are expressed. Such fermentation conditions are well known in the art. The polypeptides are then purified from the culture. These purification methods are also well known in the art.

To enhance the potential for proper post-translation modification of recombinant proteins, such as glycosylation, a baculovirus/insect cell system was chosen for expression of recombinant bovine mCD14 and sCD14 (O'Reilly et al., 1994. *Baculovirus Expression Vectors: A Laboratory Manual*, W. H. Freeman, New York, N.Y.). Glycosylation of CD14 is important for its full functional activity. The presence of sugar has been shown to inhibit CD14-mediated phagocytosis of *E. coli* (Paape et al., supra). In addition, different glycosylated isoforms of native CD14 isolated from human serum and of recombinant human sCD14 have been reported (Stelter et al. 1996. *Eur. J. Biochem*. 236: 457-464). Our data demonstrated that recombinant bovine mCD14 was expressed on the cell surface of infected insect cells through a GPI linkage, similar to what has been reported for human monocytes (Haziot, 1988, supra). The truncation of C-terminal amino acids disrupted this GPI linkage, and resulted in secretion of the protein into the culture media. Similar findings were also reported using a baculovirus/insect cell expression system for generation of human mCD14 and sCD14 (Haziot, 1994, supra; Tapping et al. 1997. *J. Biol. Chem*. 272: 23157-23164).

While recombinant DNA techniques are the preferred method of producing the polypeptides of this invention having a sequence of more than 20 amino acids, shorter polypeptides encompassed by this invention having less than about 20 amino acids are preferably produced by conventional chemical synthesis techniques and may be made in a variety of ways. Synthetically produced polypeptides of this invention can advantageously be obtained in extremely high yields and be easily purified. Suitable techniques are well known in the art, and include those described by Merrifield (1973. *Chem. Polypeptides*, Katsoyannis and Panayotis, Eds., pages 335-61; Merrifield. 1963. *J. Am. Chem. Soc*. 85: 2149, Davis et al. (1985. *Biochem. Int'l*. 10: 394-414), Stewart and Young. (1969. *Solid Phase Peptide Synthesis*), U.S. Pat. No. 3,941,763, Finn et al. (1976. In: *The Proteins*, 3rd ed., Vol. 2: 105-253), and Erickson et al. (1976. In: The Proteins, 3rd ed., Vol. 2: 257-527). In a preferred embodiment of this invention, the shorter polypeptides are synthesized by solution phase or solid phase polypeptide synthesis and, optionally, digested with carboxypeptidase (to remove C-terminal amino acids) or degraded by manual Edman degradation (to remove N-terminal amino acids). Proper folding of the polypeptides may be achieved under oxidative conditions which favor disulfide bridge formation, as described by S. B. H. Kent (1988. *Ann. Rev. Biochem*. 57: 957-89. Polypeptides produced in this way may then be purified by separation techniques widely known in the art, preferably utilizing reverse phase HPLC. The use of solution phase synthesis advantageously allows for the direct addition of certain derivatized amino acids to the growing polypeptide chain, such as the O-sulfate ester of tyrosine. This obviates the need for a subsequent derivatization step to modify any residue of the polypeptides of this invention.

The biological activity of the polypeptides of this invention, including variants, can be screened in an appropriate bioassay, as described herein. For example, binding of LPS to CD14 or a polypeptide of this invention may be measured in a standard competitive binding assay. The ability of a rbosCD14 polypeptide of the invention to block CD14/LPS interaction, may be assayed using a simple cell binding assay that permits evaluation of their effect on binding of FITC-LPS to cells expressing mCD14 or on LPS-induced CD18 expression (see Examples 4 and 5, below). Also, activity to reduce cellular inflammatory responses may be measured in terms of TNFα production by cells, as described herein.

The polypeptides of this invention are expected to have the ability to bind to LPS. This binding renders LPS unable to bind to membrane CD14 (mCD14) on macrophages and therefore results in an anti-inflammatory response in a mammal. They are also expected to bind to cellular components of gram positive cells that cause inflammation. Additionally, the polypeptides of this invention have increased ability to initiate an immune response in cells lacking mCD14, such as endothelial and epithelial cells. "Binding" to LPS means that in a standard competition assay, the polypeptide is capable of inhibiting 50% binding of CD14 to LPS between 1 mM and 1 nM, preferably 100 PM to 10 nM ($IC_{50}$ values). A standard binding assay may be carried out as is well known in the art.

The polypeptides of this invention may be used in any of a number of situations where LPS/gram positive cell component binding is required. For example, therapeutically and prophylactically, the polypeptides may be used for bovine mastitis. Thus, the novel polypeptides are useful for the prophylaxis or treatment of mastitis in mammals at doses of about 0.1 to 100 mg/kg of body weight, preferably at a level of about 1 to 50 mg/kg of body weight, and the amount may be administered, e.g., in divided doses on daily basis. The polypeptides may be administered prophylactically to individuals who may be exposed to or have been exposed to organisms which may cause mastitis or to detoxify LPS (bacterial endotoxins) by the use of the same dose set forth above in vivo; in vitro detoxification or prevention of endotoxin contamination may be carried out at a level which is effective to achieve the desired result. The amount may be based on routine experimentation based on the premise that about 1 mole of endotoxin is bound by 1 mole of polypeptide. The particular dose of a particular polypeptide may be varied within or without the range that is specified herein depending on the particular application or severity of a disease and the condition of the host. Those who are skilled in the art may ascertain the proper dose using standard procedures.

The polypeptides and fusion proteins of this invention can also be used in therapeutic compositions to inhibit formation of the mCD14/LPS or rbomCD14/LPS complex, when such formation contributes to a pathological state. Alternatively, they may be used therapeutically to mimic the role of sCD14 in initiating one or more of the functional responses dependent on the formation of the mCD14/LPS or rbomCD14/LPS complex or of the sCD14/LPS or rbosCD14/LPS complex. Thus, the polypeptides and fusion proteins of this invention may be used in the treatment of acute and chronic inflammation and for immunomodulation, including treatment of such diseases as mastitis.

In these respects, it is recognized that molecules involved in receptor-ligand interactions are generally more effective in eliciting a particular response from a cell when the molecules are present in a multimeric form as opposed to a monomeric form of the same protein. Multimeric forms of receptor proteins appear to more closely mimic the typical situation in vivo where, e.g., an effector cell will exhibit hundreds or thousands of copies of a particular receptor on its surface which then bind to the many copies of its ligand.

A variety of methods are known in the art to form multimeric forms of protein monomers. Such methods include using crosslinking agents, e.g., glutaraldehyde (e.g., Reichlin, Methods Enzymol., 70, pp. 159-65 (1980)). If thiol residues are present on a polypeptide or polypeptides, such groups may be oxidized to form intermolecular disulfide bonds to achieve multimeric forms of the polypeptide or polypeptides. Thiol residues or thiol-reactive groups may be introduced into a polypeptide using iminothiolane or heterobifunctional cross-linkers, such as N-succinimidyl-3-(2-pyridyldithio) propionate (SPDP), which contains an amine-reactive group and a thiol-reactive group. Coupling of the proteins may then be accomplished through disulfide bonds formed either directly or through homobifunctional cross-linking agents (see, e.g., Srinivasachar et al. 1989. *Biochem.* 28: 2501-09; Ramakrishnan et al. 1984. *Cancer Res.* 44: 201-08; Lambert et al. 1985. *J. Biol. Chem.* 260: 12035-41). The effectiveness of disulfide bond formation between molecules would of course be limited to the number of thiols available on the polypeptide (naturally occurring or introduced by derivatization as above) and whether such disulfide bond formation adversely affected the affinity of the resulting multimeric form. If polypeptides or proteins possess carbohydrate groups, such as in glycoproteins, the sugar moieties of such groups may be used in reactions to link one molecule with another (e.g., Liao et al. 1973. *J. Biol. Chem.* 248: 8247-53; Moroney et al. 1987. *Biochem.* 26: 8390-98).

Alternatively, multiple copies of monomers of polypeptides and fusion proteins of this invention may be bound to another molecule or substrate or particle. As in the case of the binding of LF08 to Affigel-10 beads (see infra), the formation and use of molecules, compounds or particles comprising multiple LPS-binding domains are within the scope of this invention.

In addition, this invention also includes multimeric forms of rbosCD14-Ig fusion proteins. Such multimers may be generated by using those Fc regions, or portions thereof, of Ig molecules which are usually multivalent, e.g., IgM pentamers and IgA dimers. It is of course understood that a J chain polypeptide may be necessary to form and stabilize IgM pentamers and IgA dimers. Alternatively, multimers of rbosCD14-Ig fusion proteins may be formed by using a protein with an affinity to the Fc region of Ig molecules, such as Protein A. For example, a plurality of rbosCD14-Ig fusion proteins may be bound to Protein A-agarose beads to form agarose beads whose surfaces are covered with multiple functional LPS-binding domains of the attached rbosCD14-Ig fusion proteins.

In another embodiment, this invention provides multimeric proteins capable of binding to LPS, which comprise (a) two or more of the LPS-binding polypeptides described herein, (b) two or more of the LPS-binding fusion proteins described herein, or (c) one or more of the LPS-binding polypeptides and one or more of the LPS-binding fusion proteins.

Further, rbosCD14 is useful as a reagent for generating bovine CD14-specific antibodies and for detecting bovine CD14-specific antibodies. The peptides and proteins of this invention can be used as immunogens to generate antibodies that are selectively specific for bovine sCD14. Thus, rbosCD14 can be used to generate monoclonal and polyclonal antibodies and hyperimmune serum and hyperimmune colostrum.

The term "antibody," as used herein, includes, but is not limited to a polypeptide substantially encoded by an immunoglobulin gene or immunoglobulin genes, or fragments thereof which specifically bind and recognize an analyte (antigen). Examples include polyclonal, monoclonal, chimeric, humanized, CDR-grafted, and single chain antibodies, and the like. Fragments of immunoglobulins, including Fab fragments and fragments produced by an expression library, including phage display. See, e.g., Paul, Fundamental Immunology, Third Ed., 1993, Raven Press, New York, for antibody structure and terminology.

The phrases "specifically binds to" or "specifically immunoreactive with", when referring to an antibody or other binding moiety refers to a binding reaction which is determinative of the presence of the target analyte in the presence of a heterogeneous population of proteins and other biologics. Thus, under designated assay conditions, the specified binding moieties bind preferentially to a particular target analyte and do not bind in a significant amount to other components present in a test sample. Specific binding to a target analyte under such conditions may require a binding moiety that is selected for its specificity for a particular target analyte. A variety of immunoassay formats may be used to select antibodies specifically immunoreactive with a particular protein. For example, solid-phase ELISA immunoassays are routinely used to select monoclonal antibodies specifically immunoreactive with an analyte. See Harlow and Lane (1988) Antibodies, A Laboratory Manual, Cold Spring Harbor Publications, New York, for a description of immunoassay formats and conditions that can be used to determine specific immuno-reactivity. Typically a specific or selective reaction will be at least twice background signal to noise and more typically more than 10 to 100 times background.

Another embodiment of this invention involves the use of the LPS-binding polypeptides and fusion proteins to obtain antibodies recognizing the LPS-binding domain of rbosCD14. Both monoclonal antibodies and polyclonal antibodies highly specific to the LPS-binding domain of rbosCD14 may be obtained utilizing the polypeptides and fusion proteins of this invention.

To prepare antibodies, a host animal is immunized using the rbosCD14 polypeptides of the invention or rbosCD14 fusion proteins or fragments of rbosCD14 capable of binding LPS as the immunogen. The host serum or plasma is collected following an appropriate time interval to provide a composition comprising antibodies reactive with the immunogen. Methods of antibody (polyclonal and monoclonal) production and isolation are well known in the art. See, for example, Harlow et al. 1988, supra. Purification methods may include salt precipitation (for example, with ammonium sulfate), ion exchange chromatography (for example, on a cationic or anionic exchange column run at neutral pH and eluted with step gradients of increasing ionic strength), gel filtration chromatography (including gel filtration HPLC), and chromatography on affinity resins such as protein A, protein G, hydroxyapatite, and anti-antibody.

It is also necessary to be able to screen the potentially numerous clones of hybridomas generated from the fusions in, order to identify those clones which produce antibodies which are specific for bovine CD14 and for the LPS-binding domain of the rbosCD14 polypeptide of the invention. For example, such screens may involve assaying the supernatants of cultures of hybridomas for the ability to specifically bind to rbosCD14 or to inhibit FITC-LPS from binding to bovine mCD14- or rbomCD14-expressing cells. Assays which have been used to screen hybridomas for the production of mAbs specific for rbosCD14 are applicable as primary screens for hybridomas producing mAbs specific for the LPS-binding domain of rbosCD14.

When a haptenic peptide of rbosCD14 protein is used, (i.e., a peptide which reacts with rbosCD14-specific antibodies, but cannot itself elicit an immune response), it can be conjugated to an immunogenic carrier molecule. For example, an oligopeptide containing one or more epitopes of rbosCD14 proteins may be haptenic. Conjugation to an immunogenic carrier can render the oligopeptide immunogenic. Preferred carrier proteins for the haptenic peptides of rbosCD14 are tetanus toxin or toxoid, diphtheria toxin or toxoid and any mutant forms of these proteins such as $CRM_{197}$. Others include exotoxin A of Pseudomonas, heat labile toxin of E. coli and rotaviral particles (including rotavirus and VP6 particles). Alternatively, a fragment or epitope of the carrier protein or other immunogenic protein can be used. For example, the hapten can be coupled to a T cell epitope of a bacterial toxin. See U.S. Pat. Nos. 5,785,973 and 5,601,831, the teachings of which are incorporated herein. In addition, immunogenicity of rbosCD14 could be increased by conjugation of a carrier molecule, for example, dipalmityl lysine. (See Hopp, 1984. Mol. Immunol. 21: 13-16, incorporated herein by reference.)

The DNA encoding the rbosCD14 polypeptides of this invention may also be used to prepare labeled oligonucleotide probes using techniques known in the art, such as automated synthesis. The particular nucleotide sequences selected are chosen so as to correspond to codons encoding an amino acid sequence of the rbosCD14 polypeptides of the invention. While the exact length of the probe is not critical, it is generally recognized that probes from about 15 to about 20 base pairs are usually effective. Greater selectivity may be achieved using longer probes. The probes may be labeled with a marker, such as a radionucleotide or biotin using standard procedures, and used to screen the libraries by Southern hybridization. Procedures for the hybridization assay are described, for example, in U.S. Pat. No. 5,041,378, and in Nucleic Acid Hybridization, (Ed. Hames and Higgins) 1985, the contents of each of which are incorporated by reference herein. Once a clone from the screened library has been identified by positive hybridization, it can be confirmed by methods such as restriction enzyme analysis and DNA sequencing that the clone contains a gene that encodes the amino acid sequence comprising all or part of SEQ ID NO:2 or a homologous amino acid sequence.

For RT-PCR, mRNA is transcribed into cDNA using a gene specific primer (or oligo dT if the gene sequence is unknown) and reverse transcriptase. After the first strand cDNA is produced (the RT reaction), the second DNA strand is generated using an upstream gene specific primer. This second reaction, i.e., the PCR part, with downstream and upstream primers is repeated 25-35 times to produce a DNA fragment originating from the mRNA.

The rbosCD14 polypeptides and fusion proteins of this invention may be formulated as pharmaceutical compositions using conventional methods to prepare pharmaceutically useful compositions and combinations. Herein, "pharmaceutical compositions" and "pharmaceutically useful compositions" encompass compositions used in veterinary medicine. Such compositions preferably include at least one pharmaceutically acceptable carrier. Typical carriers are aqueous carriers such as water, buffered aqueous solutions, aqueous alcoholic mixtures, and the like. Examples of such carriers are known in the art and need therefore not be provided herein, See, e.g., Remington's Pharmaceutical Sciences, (E. W. Martin). Pharmaceutical compositions of the present invention typically contain, in addition to the active polypeptide, a pharmaceutically acceptable buffer, preferably phosphate buffered saline, together with a pharmaceutically acceptable compound for adjusting isotonic pressure, such as sodium chloride, mannitol or sorbitol. The pharmaceutically acceptable compositions and methods of this invention are characterized by pharmaceutically effective amounts of a polypeptide according to the invention.

Typically, such pharmaceuticals are prepared as injectables: either as liquid solutions or suspensions, solid forms suitable for solution in, or suspension in, liquid prior to injection may also be prepared. The rbosCD14 protein preparation could also be emulsified. The peptides may be administered to a target bovine animal by any convenient route, such as subcutaneously, intraperitoneally, intramuscularly, intradermally, intravenously, intra-articularly, orally, intranasally, or preferably intramammarily, in the presence of a physiologically acceptable diluent. The proteins may be administered in a single dose, in a plurality of doses, or by continued infusion.

The proteins of the present invention may be stored under refrigeration or in frozen or lyophilized form. The proteins are administered to the target animal in an amount effective to elicit a protective effect against LPS, as compared to a control. The effective amount will vary with the particular target animal, its age and size, and may be readily determined by the practitioner skilled in the art. Suitable regimes for initial administration and booster shots will also be variable, but may be typified by an initial administration followed by subsequent inoculations or other administrations.

The term "combination" as used herein, includes a single dosage form containing at least one polypeptide of this invention and at least one other pharmaceutically active agent, a multiple dosage form wherein the polypeptide and the other active agent are administered separately, but concurrently, or a multiple dosage form wherein the two components are administered separately but sequentially. Alternatively, the polypeptides of this invention and the other active agent may be in the form of a single conjugated molecule. Conjugation of the two components may be achieved by standard cross-linking techniques well known in the art. A single molecule may also take the form of a recombinant fusion protein.

Methods for determining pharmaceutically effective dosages are known to those skilled in the art. The dosage and dose rate will depend on a variety of factors such as the specific composition, the object of the treatment, i.e., therapy or prophylaxis, method of administration, and the judgment of the treating physician.

This invention also relates to the bioanalytic use of LPS-binding polypeptides and fusion proteins, or compositions containing them, for determining the concentration of LPS proteins or the detection of LPS in a biological sample. These polypeptides and compositions may be used in a manner similar to that of reagents employed in conventional assays. In addition, the polypeptides of this invention may be utilized in diagnostic kits designed to detect the presence and measure the concentration of LPS.

In conclusion, functionally active rbosCD14 was generated in a baculovirus/insect cell expression system. The inhibitory effect of rbosCD14 on activation of PMN and the increase in level of steady TNF-α mRNA by LPS may be beneficial to animals suffering acute endotoxin shock. In addition, sensitization of the mammary gland to LPS through the effects of rbosCD14 should be beneficial to the host because a faster recruitment of leukocytes may be induced when just a few bacteria are present in the mammary gland.

EXAMPLES

The following examples serve as further description of the invention and methods for practicing the invention. They are not intended as being limiting, rather as providing guidelines on how the invention may be practiced.

Example 1

Cloning, Expression, and Purification of Recombinant Bovine Membrane CD14 and Recombinant Bovine Soluble CD14

Total RNA from the lung of a Holstein cow was isolated using Tri-reagent (Sigma, St. Louis, Mo.) according to the manufacturer's instructions. First strand cDNA was synthesized using Superscript RT II system (GIBCO-BRL Life Technologies, Gaithersburg, Md.) with an oligo(dT) primer. The cDNA coding the membrane bound (full length) bovine CD14 was PCR amplified using the sense primer boCD14F1 (5'-AAA GMTTCATGGTGTGCGTGCCCTACC-3'; SEQ ID NO:3), and the antisense primer boCD14R (5'-AAAAAGCTTACGCGAAGCCTCGGGCTCCTTGAAG-3'; SEQ ID NO:4). The boCD14 F1 and boCD14 R primers contained EcoRI and HindIII restriction sites, respectively, which permitted digestion of the PCR fragment with the cognate enzyme and subcloning into pUC18 vector (GIBCO-BRL Life Technologies). One clone, designated pBoCD14, was picked and its sequence was confirmed by automated sequencing.

The full length cDNA of bovine CD14 (rbomCD14) was subcloned into the EcoRI/HindIII site of the pBlueBac 4.5 transfer vector (Invitrogen, Carlsbad, Calif.). The pBlueBac4.5/CD14 transfer vector and Blue-N-Bac DNA (Invitrogen) were co-transfected into sf-9 insect cells to generate a recombinant virus containing rbomCD14.

The rbosCD14 construct that had a deletion of 29 amino acids of the C-terminal end was generated by PCR of pBoCD14. pBoCD14 was amplified using primers boCD14 μl and the antisense primer boCD14R2 (5'-GGAGAC-CATGGGGTCATTTTGGTG-3'; SEQ ID NO:5). The boCD14F1 and boCD14R2 primers contained EcoRI and NcoI restriction sites, respectively, which permitted digestion of the PCR fragment with the cognate enzyme and subcloning into modified pBlueBac 4.5 vector. The transfer vector pBlueBac 4.5 was modified by incorporating a NcoI site and six histidine residues before the HindIII multiple cloning site. The rbosCD14 was subcloned into the modified pBlueBac4.5 transfer vector. One clone designated clone 36 was confirmed to contain the N-terminal 1-344 amino acids of bovine CD14 by automated sequencing. The amino acid in position 343 of SEQ ID NO:2 is valine in place of isoleucine, the amino acid found in naturally occurring full length bomCD14. The substitution of valine for isoleucine results from changing the atc codon to gtc to create the NcoI restriction site. The recombinant virus containing rbosCD14 was generated and screened as described (O'Reilly, supra).

The sf-9 cells or "high five" cells (BTI-TN-5B1-4) at a density of $2\times10^6$ cells/ml were infected with virus containing rbosCD14 at a multiplicity of infection (MOI) of 10. To determine the time course of expression of rbosCD14, culture supernatant (1 ml) was collected at 0 (infection), +24, +48, +72, +96, +120 hr post infection, and assayed for the presence and amount of rbosCD14 by Western blot.

Figure 2:
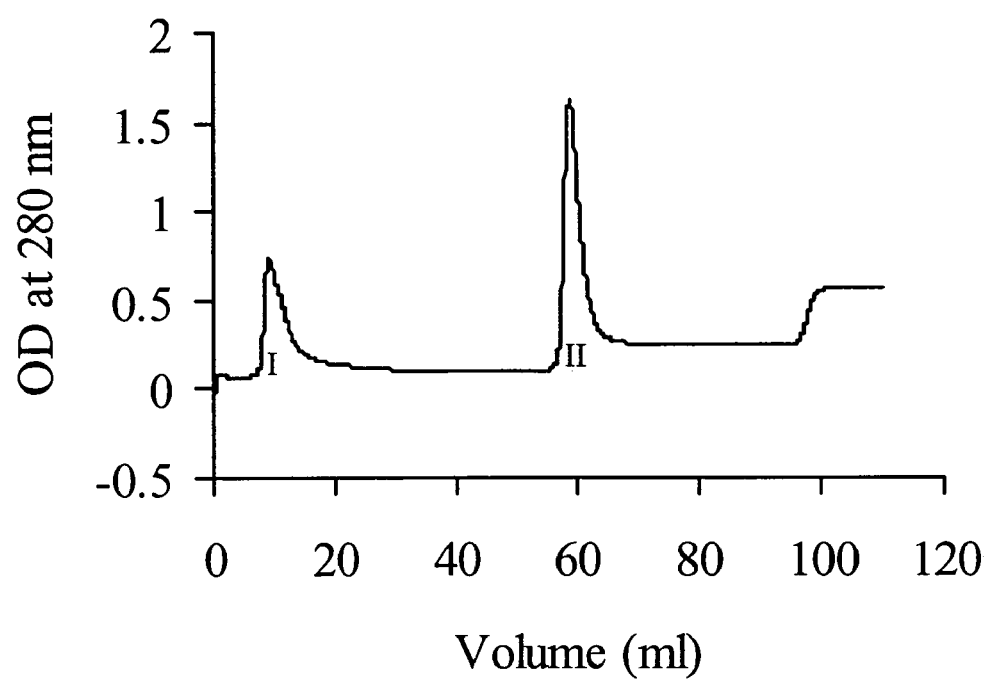
FIG. 2 shows the purification profile of rbosCD14 using Ni-NTA superflow agarose beads (Qiagen) using FPLC. The culture supernatant of infected sf-9 cells was dialyzed against PBS and buffer A, and incubated with Ni-NTA beads in the presence of 10 mM imidazole at room temperature for 3 hr. The Ni-NTA beads were packed into a XK16/20 column. The column was washed with 25 mM imidazole (Fraction I) and eluted with 100 mM imidazole (Fraction II).

Purification of rbosCD14 from the culture supernatant was performed according to Tapping (supra). Briefly, the culture supernatant was collected at various time points post infection. When infecting sf-9 cells at a density of $1.7 \times 10^6$ cells/ml with a MOI of 10, the maximal concentrations of rbosCD14 occurred 96 hr pi (FIG. 1). The supernatant was first centrifuged (100×g for 5 min), further centrifuged (6000×g for 10 min), and filtered through a 0.22 μm filter. The supernatant was dialyzed (4° C., overnight) against 0.0132 M phosphate buffered saline (PBS, pH 7.4) and buffer A (100 mM sodium phosphate, 300 mM sodium chloride, pH 8.0) in a dialysis tube with a molecular weight cutoff at 10,000-12,000 Dalton (Spectrum Laboratories, Inc., Rancho Dominguez, Calif.). The dialyzed culture supernatant was incubated with Ni-NTA superflow agarose beads (Qiagen, Valencia, Calif.) in the presence of 10 mM imidazole at room temperature for 3 hr on an orbital shaker set at 150 rpm. The Ni-NTA beads were packed into Xk16/20 column (Amersham Pharmacia, Pitscataway, N.J.). The column was connected to an FPLC (Pharmacia), washed with a 10× column volume of buffer A containing 25 mM imidazole, and rbosCD14 was eluted with 100 mM of imidazole in buffer A. Fractions (4 ml) were collected using a FRAC-200 fraction collector (Pharmacia) and analyzed for CD14 by SDS-PAGE and Western blot. Typical yields of rbosCD14 from this system was 4-6 mg/l of culture supernatant (FIG. 2).

Example 2

Detection of sCD14 in Cell Supernatants, FPLC Fractions, and Milk Whey by SDS PAGE and Western Blot The presence, purity, and amount of rbosCD14 in selected FPLC fractions was assayed by SDS-PAGE and Western blot. Twenty microliter of culture supernatant or FPLC fraction was combined with 20 μl of 2× sample loading buffer (Novex, San Diego, Calif.), and heated at 70° C. for 10 min. For samples originating from supernatants or fractions, samples (15 μl/lane) were loaded onto two 4-12% NuPAGE gels (Novex), and separated according to the manufacturer's instructions. After gel electrophoresis, one gel was silver stained and dried, and the other gel was transferred to nitrocellulose (NC) membrane (Biorad, Hercules, Calif.). The NC membranes were blocked with 1% bovine serum albumin (BSA, Sigma) in PBS containing 0.01% Tween 20 (PBS-T) at room temperature for 60 min with gentle rocking. After blocking, the NC membrane was incubated with anti-tetra-His mAb (Qiagen) or anti-ovine CD14 mAb (Serotec) for 60 min at room temperature. The NC membrane was washed three times with PBS-T and incubated with alkaline phosphatase-labeled goat-anti-mouse IgG antibody (Kirkegaard & Perry Labs Inc., Gaithersburg, Md.) for 30 min. After two washes with PBS-T and two washes with 0.85% sodium chloride, the NC membrane was developed using a BCIP/NBT kit (Kirkegaard & Perry Labs Inc.).

Milk Whey:

Milk was collected aseptically from four clinically normal mid-lactation Holstein cows. Mammary glands were determined free from intramammary infection after culturing milk on blood agar plates. Milk fat was removed after centrifugation at 1000×g for 30 min at 4° C. Whey was prepared by centrifuging the skimmed milk at 10,000×g for 30 min at 4° C. The whey was stored at −70° C. until Western blot analysis.

Figure 3:
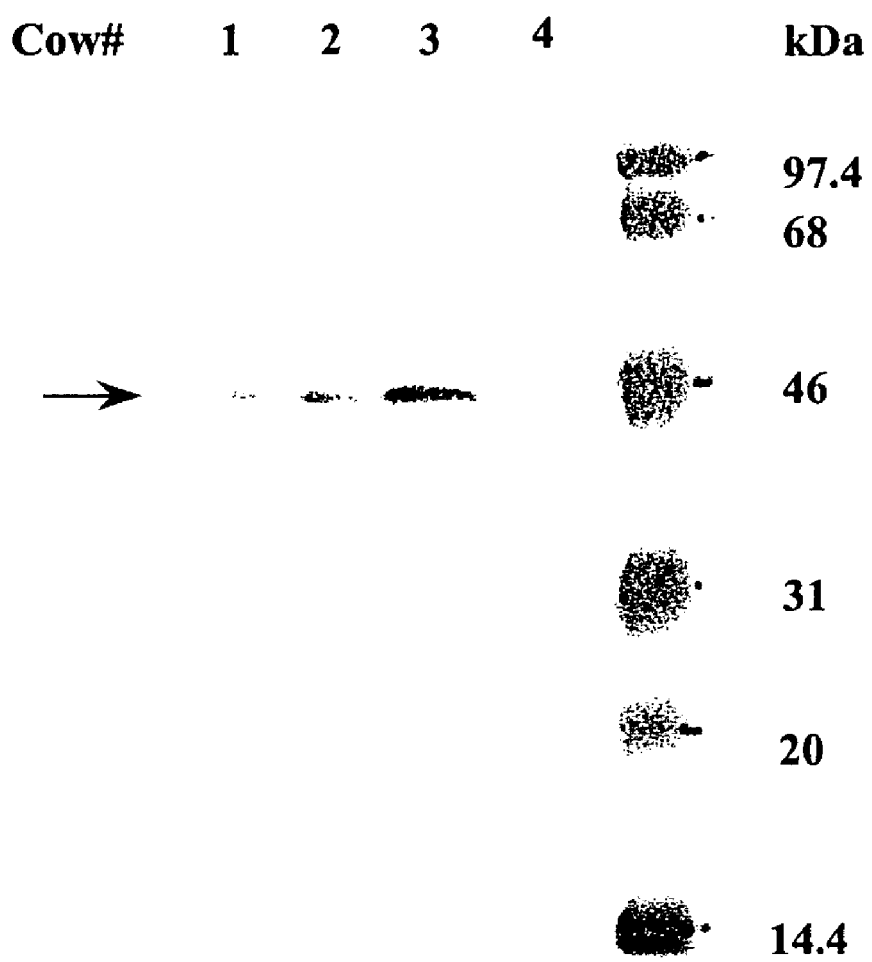
FIG. 3 depicts the presence of bovine sCD14 in whey. Proteins in whey were separated on a 10% resolving gel and transferred onto a nitrocellulose (NC) membrane. The NC membrane was probed with anti-ovine CD14 mAb.

The whey was combined with an equal volume of non-reducing 2× Lammeli buffer and heated at 70° C. for 10 min. Proteins were separated on a 10% resolving Tris-glycine gel with 4% stacking gel, and transferred onto a NC membrane. NC membranes were blocked, probed, and developed as above. A Western blot using anti-ovine CD14 mAb (IgG1) as primary antibody showed that sCD14 was present in skimmed milk with a molecular weight of 46 kD (FIG. 3). No bands were detected when blots were probed with an unrelated IgG1 mAb or secondary antibody only (data not shown).

Soluble CD14 was also detected in human milk using anti-human CD14 mAb 60bca (data not shown) by Western blot, which is consistent with Labeta et al., supra.

Example 3

Expression of Bovine CD14 on the Cell Surface of Sf-9 Insect Cells

The sf-9 insect cells expressed rbomCD14 at the cell surface, as determined by cytofluorometry. The sf-9 cells were infected with recombinant virus containing rbomCD14 at a MOI of 10. At time 0 (infection), +24, +48, and +72 hr post infection, 0.5 ml aliquots of sf-9 cells ($1.0 \times 10^6$ cells) were collected, and incubated with Rhodamine-1-(RD-1-) conjugated anti-human CD14 mAb MY4 (Coulter electronics, Hialeah, Fla.) at room temperature for 30 min. The cells were washed twice with ice-cold PBS by centrifugation at 100×g for 5 min. After the final wash, the cell pellet was resuspended in 500 μl of PBS, and analyzed for binding of anti-CD14 mAb with an EPICS Profile II® flow cytometer (Coulter Electronics, Hialeah, Fla.). The binding specificity of RD-1-labeled MY4 mAb was determined by pre-incubating cells with either unlabeled anti-human CD14 mAb 60bca (ATCC, Rockville, Md.), or anti-human CD14 mAb MY4 (Coulter) or isotype control mAb (Sigma). To determine if rbomCD14 on the cell surface of infected sf-9 cells was anchored through a glycosylated phosphatidylinositol (GPI) linkage as reported for human monocytes (Haziot, 1988, supra), the infected cells (48 hr post infection) were pre-incubated with 1 and 5 units/ml of phosphatidylinositol-specific phospholipase C PIPLC (Sigma) at 37° C. for 1 hr.

Figure 4:
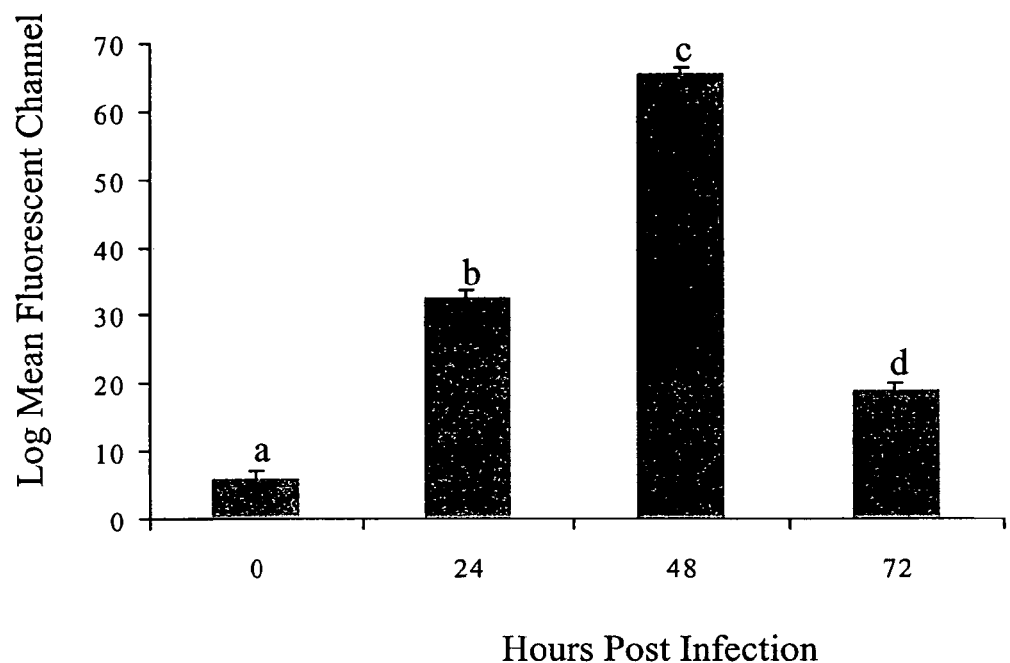
FIG. 4 shows the expression of recombinant bovine mCD14 on the cell surface of sf-9 cells infected with a recombinant virus containing the full length cDNA of bovine CD14. Aliquots of infected cells were collected at various time points post infection and expression of recombinant bovine mCD14 was determined by measuring the binding of anti-human CD14 antibody by flow cytometry.
Figure 5:
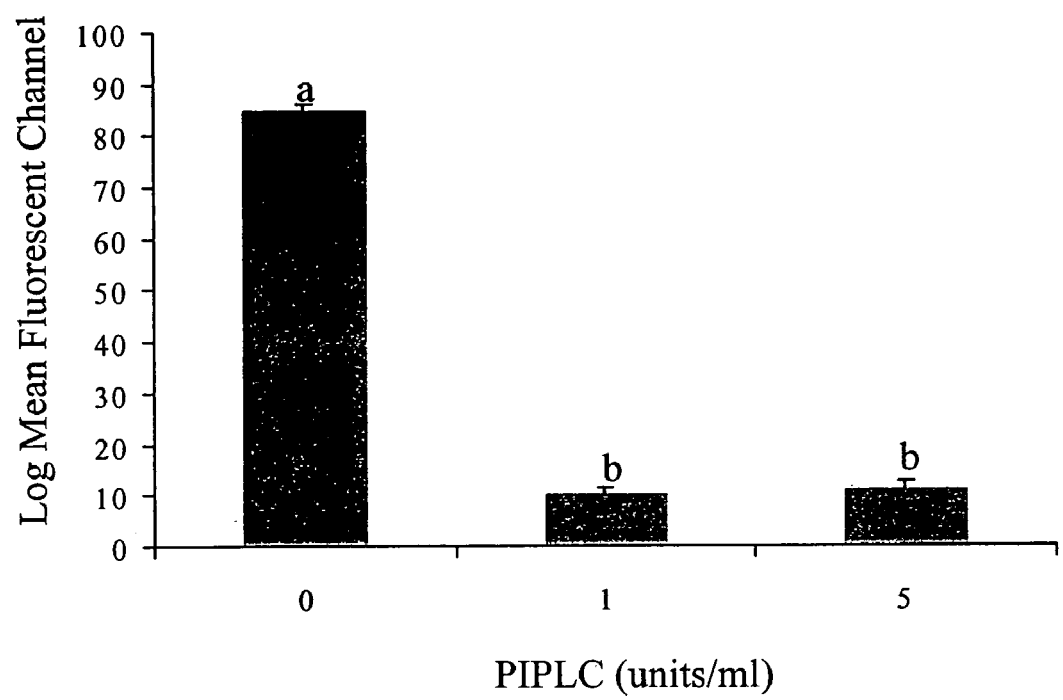
FIG. 5 shows the effect of phosphatidylinositol-specific phospholipase C (PIPLC) digestion on the binding of anti-human CD14 mAb to infected sf-9 cells. Infected sf-9 cells were collected at 48 hr post infection and incubated with 0, 1, or 5 U/ml of PIPLC at 37° C. for 55 min. The binding of mAb to PIPLC-treated cells was measured by flow cytometry. The log mean fluorescence channel was used to measure mAb binding. The data from three experiments performed in duplicate are expressed as means and standard errors; means with different letters differ (P<0.05).

The rbomCD14 was expressed on the cell surface of sf-9 cells infected with recombinant virus, but not on the cell surface of uninfected sf-9 cells (FIG. 4). Among the post infection sampling time points, infected sf-9 cells had the highest cell surface expression at 48 hr. Pre-incubating cells with unlabeled anti-human CD14 mAb MY4 or 60bca completely blocked the binding of RD-1-labeled MY4 (data not shown). Pre-incubating infected sf-9 cells (harvested at 48 hr pi) with PIPLC resulted in an 80% reduction in CD14 density on the cell surface (FIG. 5). This indicated that the full length bovine CD14 was anchored on the cell surface of sf-9 cells through a GPI-linkage. The sf-9 cells infected with virus containing the C-terminal truncated rbosCD14 of the invention did not express CD14 on their cell surface (data not shown).

Example 4

Binding of FITC-LPS to Infected Sf-9 Cells

Lipopolysaccharide binding protein has been found in the serum of humans (Schumann et al. 1990. *Science* 249: 1429-1431), rabbits (Tobias et al. 1986. *J. Exp. Med.* 164: 777-793), mice (Gallay et al. 1993. *Infect Immun.* 61: 378-383), and cows (Horadagoda et al. 1993. *Res. Vet Sci.* 55: 317-325, Khemlani et al. 1994. *J. Leukoc. Biol.* 56: 784-791), and is present in normal human serum at concentrations of 5-10 µg/ml. Its concentration may surpass 200 µg/ml during an acute phase response to bacterial infections (Tobias et al. 1992. *Am. J. Respir. Cell. Mol. Biol.* 7: 239-245). The LBP binds to LPS with high affinity (Tobias, 1986, supra), then interacts with either mCD14 or sCD14 (Wright et al. 1991. *J. Exp. Med.* 173: 1281-1286; Pugin et al., supra). The presence of LBP increases the sensitivity of cells responding to LPS (Lee et al. 1992. *J. Exp. Med.* 175: 1697-1705).

Aliquots of sf-9 cells (48 hr post infection) infected with rbomCD14-containing virus were pelleted by centrifugation (100×g for 5 min), and resuspended in Grace insect media (Quality Biological, Inc., Gaithersburg, Md.) containing either 10% fetal bovine serum (FBS), normal bovine serum (NBS), or acute phase bovine serum (APBS). NBS and APBS were obtained from blood collected at 24 hr before and 18 hr after injecting 500 µg of LPS through the teat canal and into the mammary gland cistern of a lactating cow. Cells were incubated with FITC-LPS at 4° C. for 30 min. The cells were washed twice with ice-cold PBS, resuspended in 500 µl of PBS, and analyzed by flow cytometry (Coulter) for binding of FITC-LPS. In the inhibition study, a 100-fold excess of unlabeled LPS together with FITC-LPS was added to the cells. To determine the role of rbomCD14 on the binding of LPS to cells, the cells were pre-incubated with anti-human CD14 mAb MY4 (Coulter) at 4° C. for 30 min.

Figure 6:
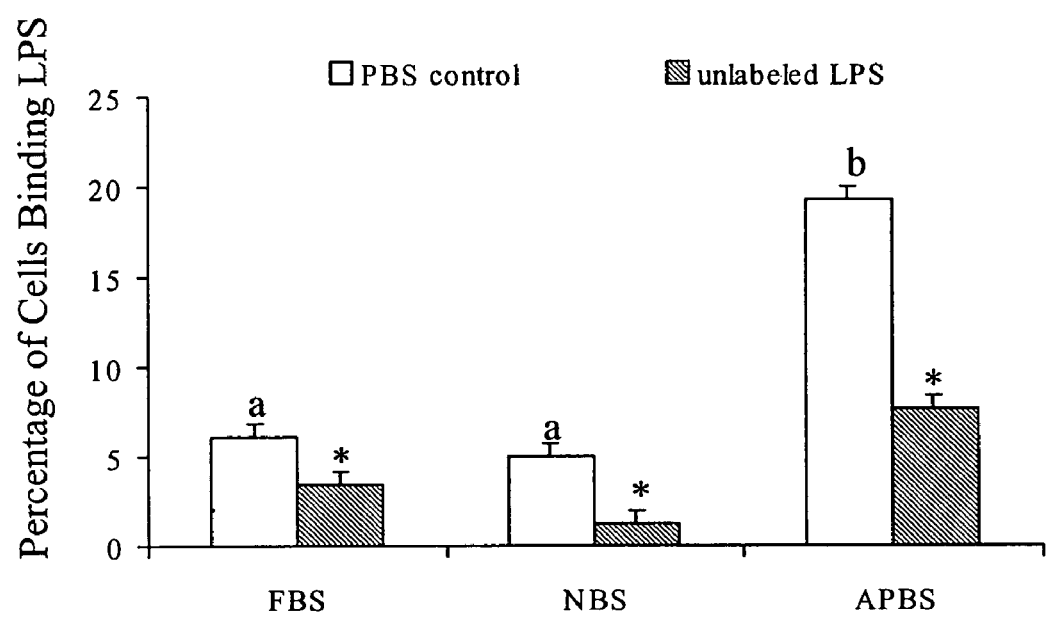
FIG. 6 illustrates binding of FITC-LPS ($10^4$ ng/ml) to infected sf-9 cells in the presence of 10% fetal bovine serum (FBS), normal bovine serum (NBS), and acute phase bovine serum (APBS) in the absence (PBS control, □) or presence (■) of 100 fold unlabeled LPS. Percentage of cells fluorescing was used as a measure for FITC-LPS binding. The data from two experiments performed in duplicate are expressed as means and standard errors. Means with different letters differ (P<0.05). *denotes that means within the same serum groups differ (P<0.05).

Binding of FITC-LPS to sf-9 cells infected with rbomCD14-containing virus was detected at a concentration of $10^4$ ng/ml in the presence of 10% FBS. At this concentration of FITC-LPS ($10^4$ ng/ml), binding to infected sf-9 cells in the presence of NBS was similar to the binding that occurred in the presence of FBS. However, the percentage of cells binding FITC-LPS was increased 3 fold in the presence of APBS when compared either to FBS or to NBS, which was prepared from blood collected from the same animal at 24 hr before injection of LPS (FIG. 6). The presence of unlabeled LPS inhibited binding of FITC-LPS to sf-9 cells in all three types of serum by 50%. The binding of FITC-LPS ($10^4$ ng/ml) to infected sf-9 cells in the presence of APBS was CD14-dependent as exemplified by a reduction in binding of FITC-LPS by 50% in the presence of anti-human CD14 mAb.

These data indicate that LBP facilitated the binding of FITC-LPS to rbomCD14 on the cell surface of infected sf-9 cells. In contrast to results with human CD14, a greater concentration of FITC-LPS ($10^4$ ng/ml) was required for significant binding to bovine mCD14 on the cell surface of infected sf-9 cells. Binding of FITC-LPS to bovine macrophages collected from involuted mammary gland secretions was also observed at $10^4$ ng/ml (unpublished observation). Others also reported binding of FITC-LPS to bovine monocytes or macrophages at concentrations of $10^3$–$2.5 \times 10^3$ ng/ml and that binding was inhibited by unlabeled LPS (Jungi, supra; Bochsler et al. 1993. *Inflammation* 17: 47-56; Grunwald et al. 1993. *Circ. Shock* 39: 220-225).

Example 5

Effect of rbosCD14 on CD18 Expression of PMN Stimulated with LPS

CD18 expression on the cell surface of PMN is a LPS-sensitive parameter. To determine whether the rbosCD14 protein produced by insect cells is functionally active, blood (100 µl) was treated with either LPS (*E. coli* 0111:B4, final concentrations of 0, 1, 10, 100 ng/ml), LPS pre-incubated with rbosCD14 (final concentrations of 10 and 100 µg/ml), or LPS pre-incubated with BSA (final concentrations of 10 and 100 µg/ml) at 37° C. in 5% $CO_2$ for 90 min. (A whole blood assay was used to more closely mimic septic shock in vivo.) The blood was then incubated with anti-bovine CD18 mAb (Dr. Jean-Jacques Letesson, Facultes Universitaires Notre-Dame de la Paix) on ice for 30 min. After lysis of red blood cells (RBC) twice with 150 µl of lysis buffer (2.6 g-Tris/100 ml water+7.4 g $NH_4Cl$/900 ml water), the leukocytes were incubated with FITC-conjugated goat-anti-mouse IgG (H+L) (Kirkegaard & Perry Labs Inc.) at 4° C. for 30 min. After washing, leukocytes were fixed in 2% paraformaldehyde. The binding of anti-bovine CD18 mAb on PMN was analyzed by flow cytometry.

Expression of CD18 on the cell surface of PMN increased when cells were treated with LPS at a concentration of 100 ng/ml (FIG. 7A). This concentration was chosen as the optimal activation concentration in subsequent studies. Pre-incubation of LPS with rbosCD14 at 10 or 100 µg/ml abolished the increase in CD18 expression induced by LPS alone. However, pre-incubation of LPS with BSA, another LPS-binding protein, had no adverse effects on the expression of CD18 on the cell surface of PMN. In addition, rbosCD14 or BSA alone at both 10 and 100 µg/ml did not affect expression of the CD18 on PMN (FIG. 7B). These results indicated that rbosCD14 generated by the baculovirus/insect cell expression system was functionally-active and capable of inhibiting the activation of PMN in whole blood stimulated by LPS.

In this study, variation among cows was observed in CD18 expression on PMN after exposure to LPS. Among the seven cows used in this study, PMN from three cows showed increased expression of CD18 after stimulation with LPS at concentrations from 1-1000 ng/ml. One of these animals responded to LPS at a concentration of only 1 ng/ml. PMN from the other four cows did not show increases in expression of CD18 even at a LPS concentration of 1000 ng/ml. Therefore, we could not evaluate effects of rbosCD14 on CD18 expression of PMN from those four cows. Others have reported cow to cow variation as well as day to day variation within individual cows (Banks et al. 1985. *Am. J. Vet Res.* 46: 1568-1572). The sensitivity of animals to LPS is genetically determined. In mice, strains that were either hypersensitive or hyposensitive to LPS were extensively studied (Vogel et al. 1999. *J. Immunol.* 162: 5666-5670). The hyposensitive strain has a point mutation in the tlr4 gene, which encodes the TLR4 receptor that mediates the activation effect of LPS on host cells. In addition, sensitivity to LPS is also affected by experimental conditions. It is known that mice treated with hepatotoxic agents, growing malignant tumors, or infected with Gram-negative or Gram-positive bacteria will have increased sensitivity to LPS (Galanos et al. 1993. *Immunobiology* 187: 346-356). Endotoxin tolerance (hyposensitivity) can also be induced by prior exposure to LPS (Galanos, supra). Thus, without further data, we cannot conclude that either genetic components or environmental conditions are the primary contributing factor to the variation observed in this study.

Example 6

Effect of rbosCD14 on Abundance of mRNA Transcripts for TNF-α, IL-6, and IL-8 Detected by Competitive RT-PCR Changes in steady mRNA levels for inflammatory cytokines in leukocytes treated with LPS were also used to evaluate the functional activity of rbosCD14. Total RNA and cDNA were derived from leukocytes in whole blood treated with LPS (10 μg/ml). A 456 bp fragment of bovine IL-6 cDNA was PCR amplified using the sense primer IL-6F1 (5'-GGGGCTGCTCCTGGTGAT-3'; SEQ ID NO:6) and the antisense primer IL-6R1 (5'-TTTGTGGCTGGAGTGGTTATTAGA-3'; SEQ ID NO:7) and cloned into the pCR2.1-TOPO vector (Invitrogen). One clone, designated as BoIL-6 native#8, was picked and confirmed to contain a 456 bp of bovine IL-6 DNA by automated sequencing. The BoIL-6 was re-amplified using the sense and anti-sense primers IL-6F2 (5'-ACTGTCGACA GAACGAGTATGAGG-GAAATC-3'; SEQ ID NO:8) and IL-6R2 (5'-GATTGTC-GACATTTT CTGCCAGTGTCTCC-3'; SEQ ID NO:9), respectively. The amplified PCR product was purified, digested with SalI, ligated, and transformed into *E. coli* DH5a cells. One clone, designated as BoIL-6M#3, was picked and confirmed to contain a 351 bp of bovine IL-6 DNA by restriction enzyme digestion and PCR amplification using IL-6F1 and IL-6R1. Therefore, BoIL-6M#3 was used as a competitor molecule to study transcriptional changes of bovine IL-6.

Competitor molecules for bovine TNF-α, IL-8, and hypoxanthine phosphoribosyl-transferase (HPRT) were constructed as previously described (Zarlenga et al. 1995. *BioTechniques* 19: 324-326). The first strand of cDNA was synthesized from 1 μg of total RNA at 37° C. for 45 min (Vanden Heuvel et al. 1993. *BioTechniques* 14: 395-398). The cDNA reaction contained 67 mM Tris-HCl (pH 8.8, Sigma), 16 mM $(NH_4)_2SO_4$ (Sigma), 0.8 μm EDTA (Sigma), 0.3% α-mercaptoethanol (Biorad), 0.1 mg/ml BSA (Calbiochem), 2.5 mM $MgCl_2$ (Perkin Elmer), 1 mM dNTP (Pharmacia), 7.5 μg/ml oligo(dT)$_{18}$ (Bioserve, Laurel, Md.), 6 units of Rnasin (Promega), and 100 units of MMLV reverse transcriptase (Promega).

The cDNAs derived from 1 μg of total RNA were normalized to HPRT levels. The normalized cDNA was PCR amplified with a constant amount of each cytokine competitor. The competitive PCR was run by co-amplifying cDNA and competitor in a reaction containing 67 mM Tris-HCl (PH 8.8), 16 mM $(NH_4)_2SO_4$, 0.8 μm EDTA, 0.3% α-mercaptoethanol, 0.1 mg/ml BSA, 1.5 mM $MgCl_2$, 200 μm dNTP, 0.25 μm each primer and 0.625 units of Amplitaq polymerase (Perkin Elmer). The PCR mixture was cycled 30 times at 94° C. for 40 sec, 55° C. for 45 sec, and 72° C. for 1 min. Primer sequences for HPRT, TNF-α, IL-6, and IL-8 are listed in Table 1. The PCR products were separated on a 2% Metaphor:GTG (1.8:0.1 wt/wt, FMC) agarose gel and stained with ethidium bromide (Sigma). The intensity of the band was determined by scanning and analyzing by a UVP gel documentation system (UVP, Inc., Upland, Calif.). For TNF-α and IL-6, ratio of the intensity between the cDNA to competitor was determined and normalized to the HPRT content. For IL-8 competitive RT-PCR, each normalized cDNA was diluted and run with 1200 fg of IL-8 competitor in a PCR. A standard curve using a fixed amount of cDNA with various amounts of IL-8 competitor was also constructed as described (Vanden Heuvel et al., supra). The calculated amount of IL-8 was used for statistical analysis.

TABLE 1

Primer sequences used in competitive RT-PCR.

| Primer Name | SEQ ID # | Primer Sequence |
|---|---|---|
| IL-6 F1 | 6 | 5'-GGGGCTGCTCCTGGTGAT-3' |
| IL-6 R1 | 7 | 5'-TTTGTGGCTGGAGTGGTTATTAGA-3' |
| IL-6 F2 | 8 | 5'-ACTGTCGACAGAACGAGTATGAGGGAAATC-3' |
| IL-6 R2 | 9 | 5'-GATTGTCGACATTTTCTGCCAGTGTCTCC-3' |
| HPRT forward | 10 | 5'-GGAGATGATCTCTCAACTTTAACTGG-3' |
| HPRT reverse | 11 | 5'-CATTATAGTCAAGGGCATATCCCAC-3' |
| TNFα forward | 12 | 5'-CAAGAATTCAGGTCCTCTTCTCAAGCCTCAAGTAAC-3' |
| TNFα reverse | 13 | 5'-TTTGGATCCCGGCAGGTTGATCTCAGCACTGAGG-3' |
| IL-8 forward | 14 | 5'-GAATTCATGACTTCCAAACTGGCTGTTGC-3' |
| IL-8 reverse | 15 | 5'-TCATGGATCTTGCTTCTCAGCTC-3' |

Whole blood (n=3 cows) was collected using sodium heparin as an anti-coagulant. Five ml of blood were incubated with 300 μl of activation medium at 37° C., 5% $CO_2$ for 2 hr. Activation medium consisted of LPS (final concentrations of 0, 1, 100, 10,000 ng/ml), LPS+rbosCD14 (10 μg/ml), LPS+BSA (endotoxin-free, 10 μg/ml), LPS+rbosCD14+anti-human CD14 mAb (10 μg/ml), or LPS+polymyxin B sulfate (10 μg/ml). All activation media were incubated at 37° C. for 1.5 hr before combining with blood. After incubation of blood with activation medium, plasma was collected following centrifugation of blood at 300×g for 5 min at 4° C., then stored at −20° C. The concentration of TNF-α in plasma was determined by radioimmunoassay as described by Kenison et al. (1990. *J. Immunoassay* 11:177-198). The RBC were lysed by incubating with 7 ml of lysis buffer on ice for 10 min. The leukocytes were pelleted at 200×g for 5 min, washed once with ice-cold PBS at 200×g for 5 min at 4° C. The cell pellet was lysed in Tri-reagent (Sigma). Total RNA was isolated according to the manufacturer's instructions. The first strand cDNA was synthesized using Superscript RT II system (GIBCO-BRL Life Technologies, Md., USA) and oligo(dt) primer.

Figure 8:
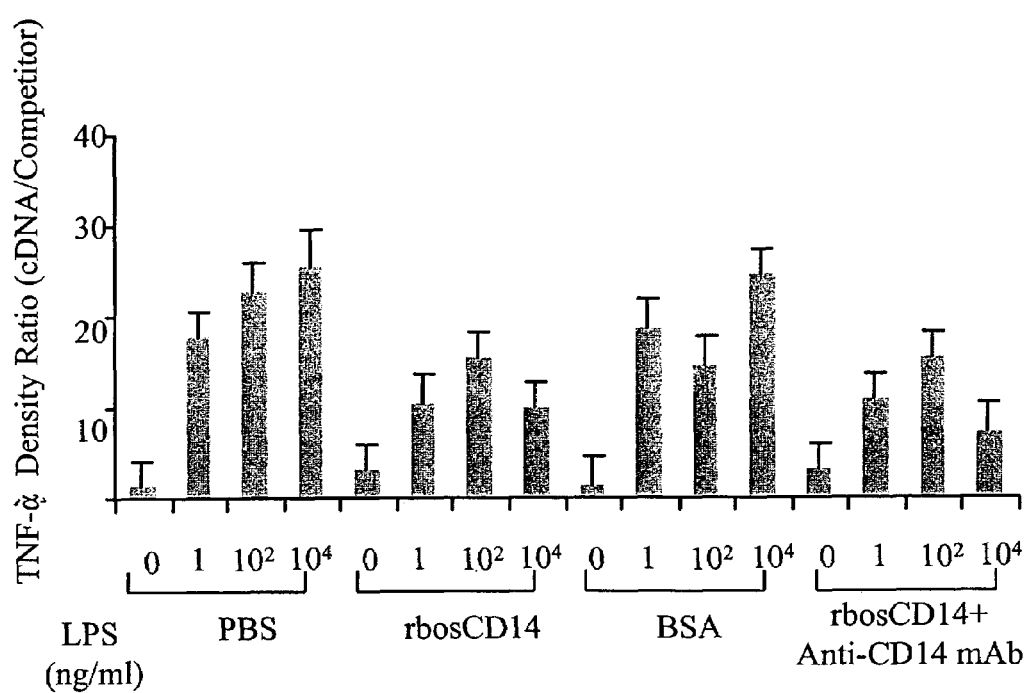
FIG. 8 shows the effect of rbosCD14 on transcription of TNF-α in leukocytes treated with LPS ex vivo. LPS was pre-incubated with PBS, rbosCD14, BSA or rbosCD14+anti-human CD14 mAb at 37° C. in 5% $CO_2$ for 60 min, and then incubated with 5 ml of blood for 2 hr. Each sample was PCR amplified in triplicate. The data from three cows are expressed as means and standard errors.
Figure 9:
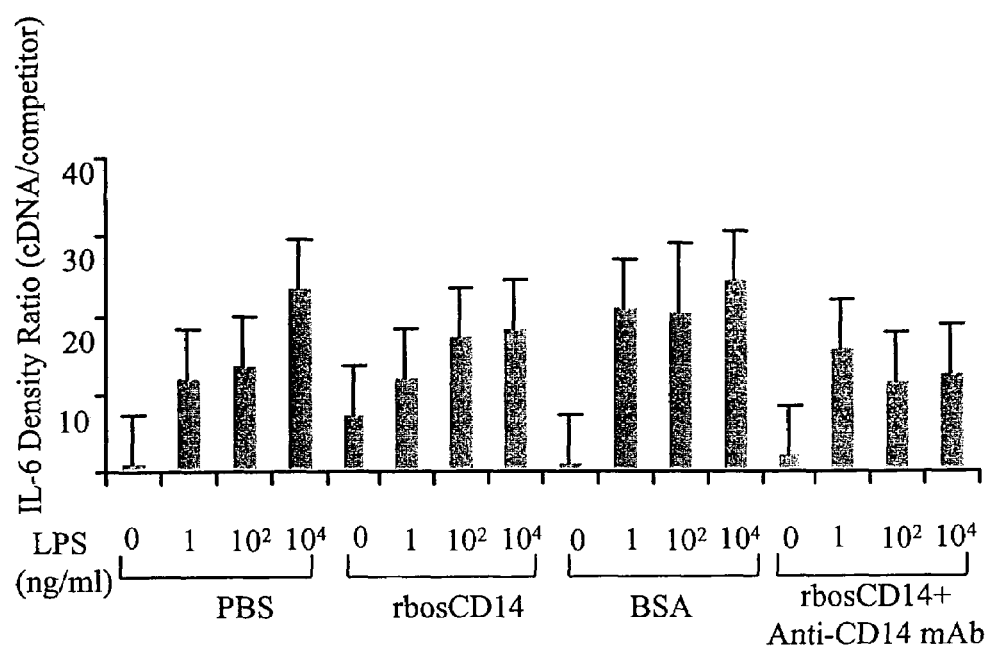
FIG. 9 illustrates the effect of rbosCD14 on transcription of IL-6 in leukocytes treated with LPS ex vivo. LPS was pre-incubated with PBS, rbosCD14, BSA, or rbosCD14+anti-human CD14 mAb at 37° C. in 5% $CO_2$ for 60 min, and then incubated with 5 ml of blood for 2 hr. Each sample was PCR amplified in triplicate. The data from three cows are expressed as means and standard errors.
Figure 10:
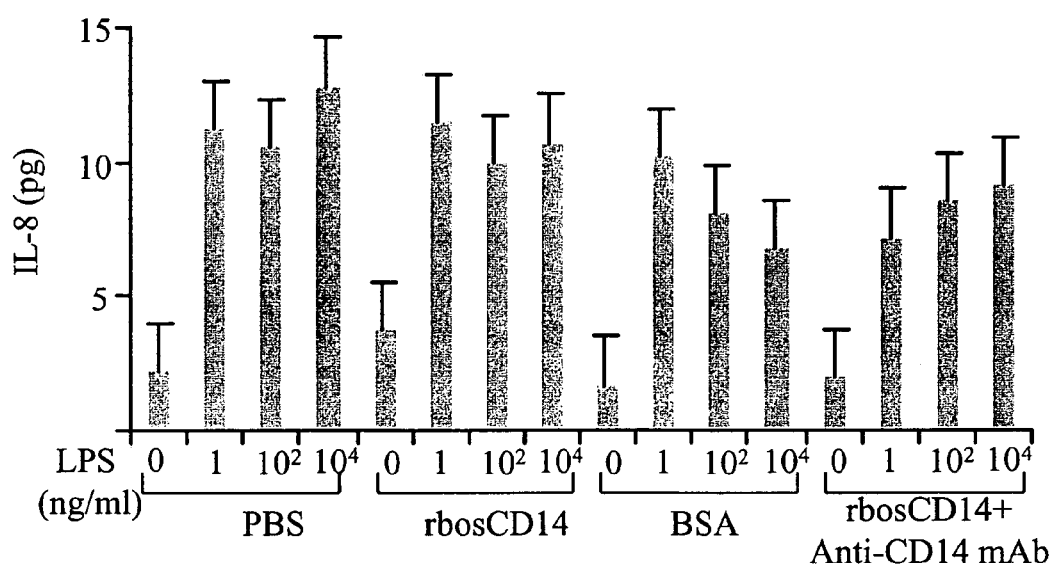
FIG. 10 shows the effect of rbosCD14 on transcription of IL-8 in leukocytes treated with LPS ex vivo. LPS was pre-incubated with PBS, rbosCD14, BSA, or rbosCD14+anti-human CD14 mAb at 37° C. in 5% $CO_2$ for 60 min, and then incubated with 5 ml of blood for 2 hr. Changes in transcription of IL-8 in leukocytes were measured by competitive RT-PCR; data presented reflect the calculated amount of IL-8. Each sample was PCR amplified in triplicate. The data from three cows are expressed as means and standard errors.

Whole blood treated with LPS at concentrations of 1, 100, or $10^4$ ng/ml resulted in an increase in the transcription of mRNA for TNF-α, IL-6, and IL-8 in leukocytes ($P<0.05$); however, the transcription of mRNA for each cytokine was similar across all three LPS concentrations ($P>0.05$, FIGS. 8, 9, and 10). Pre-incubation of LPS with rbosCD14 (14.1 µg/ml) inhibited the increases in steady TNF-α mRNA when compared to leukocytes treated with LPS alone (FIG. 8). This indicated that the LPS-induced increase in level of steady TNF-α in leukocytes was CD14-dependent. To verify the involvement of rbosCD14 in the inhibition of the LPS-induced increase in steady TNF-α mRNA level, rbosCD14 (14.1 µg/ml) was incubated with an excess amount of anti-human CD14 mAb (20 µg/ml) prior to adding LPS. The level of steady TNF-α mRNA remained down-regulated, indicating that the excess amount of anti-human CD14 mAb blocked the binding of LPS to mCD14 on the cell surface of monocytes and PMN in blood.

Pre-incubation of LPS with rbosCD14 (14.1 µg/ml) did not affect mRNA transcription for IL-6 and IL-8 (FIGS. 8 and 9); leukocytes treated with either LPS–rbosCD14 or LPS–rbosCD14+anti-CD14 mAb had similar levels of steady mRNA for IL-6 and IL-8 when compared to leukocytes treated with LPS alone. This suggests that the LPS-induced increase in levels of steady IL-8 and IL-6 mRNA were CD14 independent.

This CD14-independency may be due to two properties of cytokines. First, cytokines interact with each other, where TNF-α is able to induce the production of IL-6, IL-8, and IL-1 (Fong et al. 1989. *J. Exp. Med.* 170: 1627-1633). It was reported that TNF-α is secreted slightly before IL-1β and IL-8 in milk whey in experimental induced *E. coli* mastitis (Shuster et al. 1995. *Am. J. Vet Res.* 56: 313-320; Riollet et al. 2000. *Clin. Diagn. Lab. Immunol.* 7: 161-167). Second, cytokines function at minute concentrations. Biological activity of TNF-α can be observed at 0.01 ng/ml (Riollet, supra). TNF-α in plasma from blood treated with LPS (0.17 to 0.34 ng/ml) was able to induce maximal transcription of IL-6 and Il-8. Therefore, increase in level of steady IL-6 and IL-8 mRNA in leukocytes treated with LPS is at least partially induced by TNF-α.

Pre-incubation of LPS with BSA (14.1 µg/ml)-did not affect the LPS-induced changes in mRNA levels for any of the three cytokines (FIGS. 8, 9, and 10).

Example 7

Figure 11:
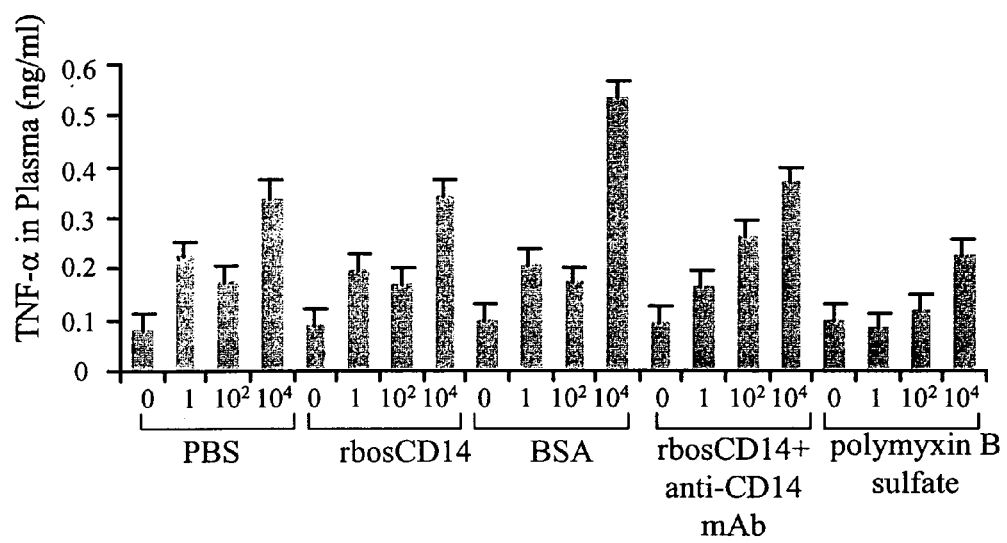
FIG. 11 illustrates the effect of rbosCD14 on the concentration of TNF-α in plasma from blood treated with LPS. LPS was pre-incubated with PBS, rbosCD14, BSA, rbosCD14+anti-CD14 mAb or polymyxin B sulfate at 37° C. in 5% $CO_2$ for 60 min, and then incubated with 5 ml of blood for 2 hr. After incubation, blood was centrifuged at 1000×g for 5 min at 4° C. Plasma was collected and stored at −20° C. until analysis. The data from three cows are expressed as means and standard errors.

Effect of rbosCD14 on Concentration of TNF-α in Plasma from Blood Treated with LPS Incubation of blood with LPS at 1,100, or $10^4$ ng/ml resulted in an increase ($P<0.05$) in plasma TNF-α by 2.8, 2.2, and 4.3 fold, respectively (FIG. 11). Plasma derived from blood treated with LPS–rbosCD14 complexes, LPS+ rbosCD14+anti-human CD14 mAb, or LPS (1 and 100 ng/ml)+BSA had similar concentrations of TNF-α when compared to plasma from blood treated with LPS alone ($P>0.05$). Pre-incubation with the highest concentration of LPS ($10^4$ ng/ml) and BSA caused a 5.4 fold increase in the concentration of TNF-α in plasma when compared to LPS ($10^4$ ng/ml) alone ($P>0.05$). Pre-incubation of LPS with polymyxin B sulfate inhibited the LPS-induced increase of plasma TNF-α level ($P>0.05$). Incubation of blood with rbosCD14, BSA, rbosCD14+anti-human CD14 mAb or polymyxin B sulfate had no effect on TNF-α levels ($P<0.05$).

Example 8

Effect of rbosCD14 on Transcription of IL-8 in Mammary Ductal Epithelial Cells Treated with LPS As discussed above, studies have shown that sCD14 forms a complex with LPS and mediates activation of human cells not bearing mCD14 in the presence of low concentrations of LPS (Pugin et al., Frey et al., supra). Others have reported the expression of cytokine mRNAs for IL-1α, IL-1β, IL-6, IL-10, TNFα, GM-CSF, and IL-8 as well as secretion of IL-1, IL-6, and IL-8 in bovine mammary epithelial cells after treatment with doses of LPS in the 1 to 20 µg/ml range in the presence of serum (Boudjellab et al. 1998. *Am. J. Vet. Res.* 59: 1563-1567; Okada et al. 1997. *J. Vet. Med. Sci.* 59: 503-507; Okada et al. 1999. *J. Vet. Med. Sci.* 61: 33-35). We measured the role of rbosCD14 in sensitizing bovine mammary epithelium to respond to low concentrations of LPS.

Epithelial cells from the ductal region of the mammary gland of a lactating cow were kindly provided by Dr. Albert Guidry (Cifrian et al. 1994. Am. J. Vet. Res. 55: 239-246). Cells were cultured on collagen-coated 60 mm dishes (Beckman Dickson) in culture medium containing 40% RPMI 1640 (Hyclone), 40% Dulbecco's modified Eagle's medium (DMEM, Hyclone), 10% fetal bovine serum (FBS, Hyclone), 1% antibiotic-antimycotic solution (Life Technology, Gaithersburg, Md.), 1 mM sodium pyruvate (Hyclone), 2 mM L-glutamine (Hyclone), 40 mM HEPES buffer (Hyclone), bovine insulin (5 µg/ml, Sigma), hydrocortisone (1 µg/ml, Sigma), and bovine prolactin (1 µg/ml, courtesy of Dr. Anthony Capuco, USDA, Beltsville, Md.).

A six well plate was coated with type I collagen solution (Beckman Dickinson) by incubating with 2 ml of collagen solution (50 µg/ml in 0.01N HCl) at room temperature for 1 hr. The collagen solution was decanted after incubation. The plate was washed twice with PBS to neutralize residual HCL. Mammary ductal epithelial cells were seeded and grown to confluence. To eliminate the effect of sCD14 in fetal bovine serum, the cell monolayer was then washed twice with PBS and cultured overnight in serum-free growth media. The monolayer was then washed twice with PBS before treatment to remove residual serum factors. Treatment media (2 ml) was added to each well. Treatment media consisted of LPS (0, 0.1, 1, 10, 100, 1000 ng/ml) or LPS–rbosCD14 (15 µg/ml) complex formed by pre-incubation overnight at 37° C. The monolayer was incubated in treatment media for 2, 6, and 24 hr. At each time point, the monolayer was washed twice with PBS and lysed in 1 ml of Trireagent (Sigma). Total RNA was isolated according to the manufacturer's instructions.

Competitive RT-PCR was used to detect changes in transcription of IL-8. Each normalized cDNA was PCR amplified with 50 fg of IL-8 competitor, and the density ratio between cDNA band and competitor band was used as the variable for comparison among samples. Under serum free conditions, cells treated with LPS at 0.1, 1, 10, 100, and 1000 ng/ml for 2 hr had a similar density ratio when compared to untreated cells, i.e., LPS alone at these concentrations did not increase transcription of IL-8. Increasing treatment time to 6 or 24 hr did not change the density ratio.

Figure 12:
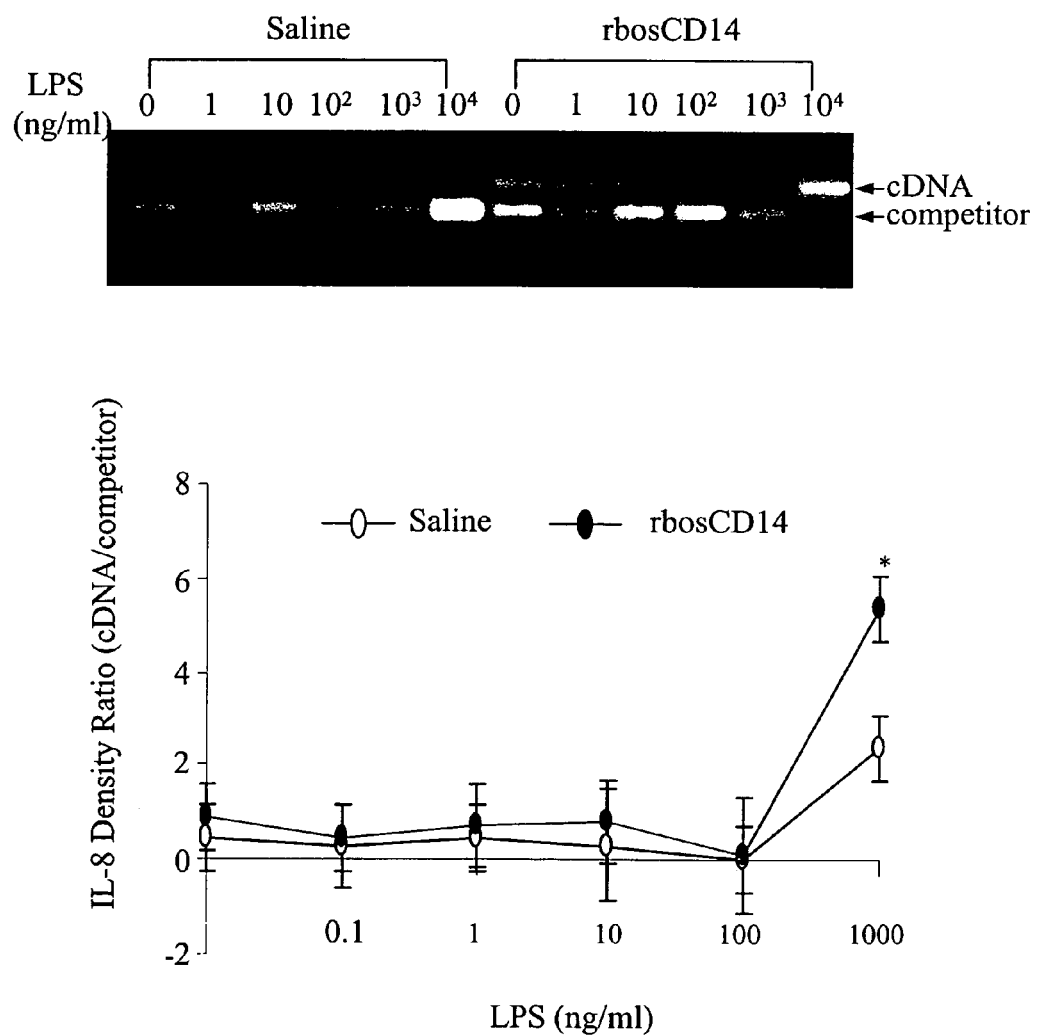
FIG. 12 shows the effect of rbosCD14 on transcription of IL-8 in mammary ductal epithelial cells treated with LPS for 2 hr. Confluent epithelial cells were incubated with LPS (0, 0.1, 1, 10, 100, 1000 ng/ml) or LPS−rbosCD14 (15 µg/ml) complex formed by incubation at 37° C. for 2 hr. The density ratio between cDNA band and competitor band after competitive RT-PCR was used to measure changes in transcription of IL-8. Each PCR was run in triplicate. The means and standard errors from three experiments are presented. *denotes that means within the LPS treatment groups differ (P<0.05).
Figure 13:
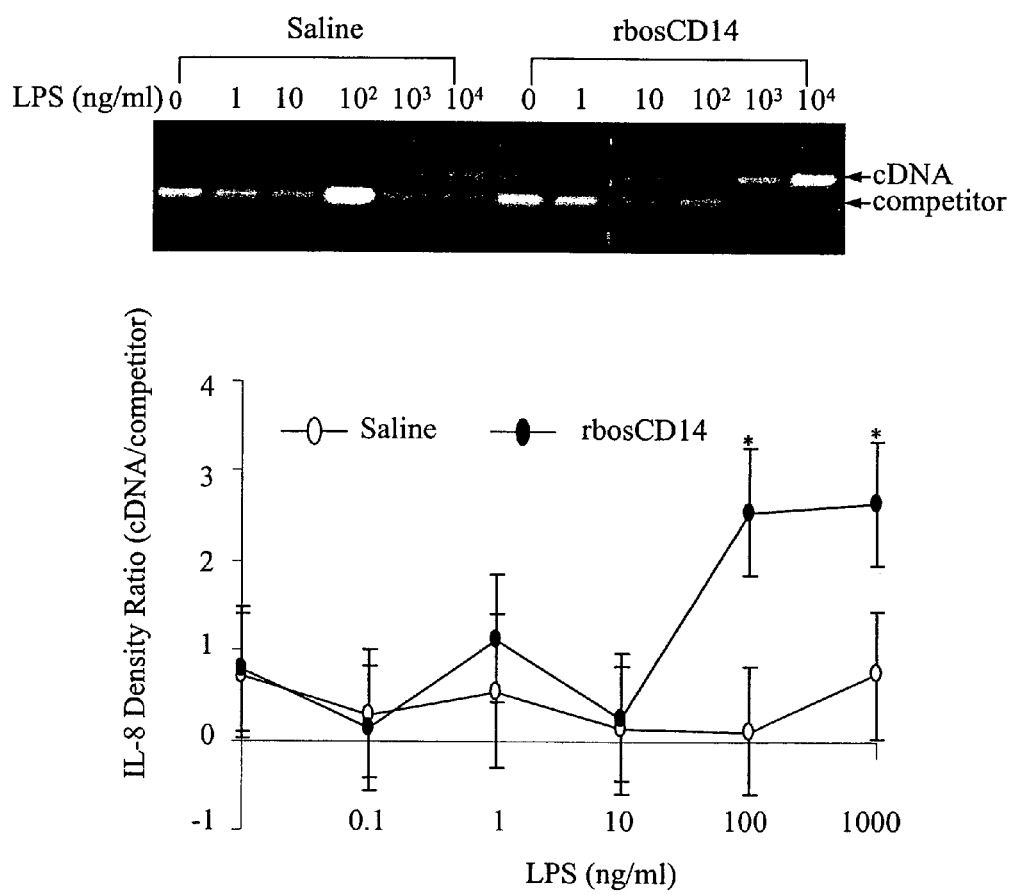
FIG. 13 shows the effect of rbosCD14 on transcription of IL-8 in mammary ductal epithelial cells treated with LPS for 6 hr. Confluent epithelial cells were incubated with LPS (0, 0.1, 1, 10, 100, 1000 ng/ml) or LPS−rbosCD14 (15 µg/ml) complex formed by incubation at 37° C. for 6 hr. The density ratio between cDNA band and competitor band after competitive RT-PCR was used to measure changes in transcription of IL-8. Each PCR was run in triplicate. The means and standard errors from three experiments are presented. *denotes that means within the LPS treatment groups differ (P<0.05).
Figure 14:
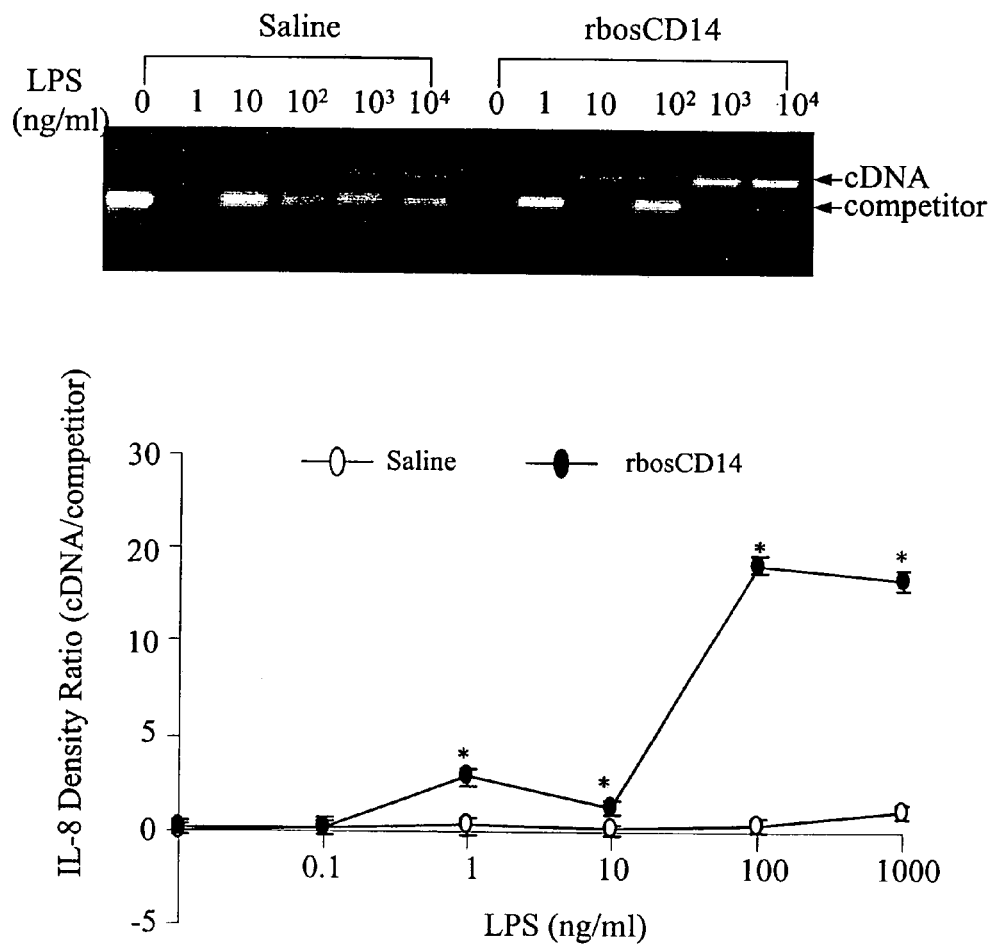
FIG. 14 shows the effect of rbosCD14 on transcription of IL-8 in mammary ductal epithelial cells treated with LPS for 24 hr. Confluent epithelial cells were incubated with LPS (0, 0.1, 1, 10, 100, 1000 ng/ml) or LPS−rbosCD14 (15 µg/ml) complex formed by incubation at 37° C. for 24 hr. The density ratio between cDNA band and competitor band after competitive RT-PCR was used to measure changes in transcription of IL-8. Each PCR was run in triplicate. The means and standard errors from three experiments are presented. *denotes that means within the LPS treatment groups differ ($P<0.05$).

In contrast, LPS (1000 ng/ml)-rbosCD14 complex induced the transcription of IL-8 after 2 hr. Cells treated with LPS–rbosCD14 complex increased the density ratio by 2.2 fold when compared to cells treated with LPS (1000 ng/ml) alone for 2 hr (P<0.05, FIG. 12). As treatment time increased to 6 and 24 hr, the LPS–rbosCD14 complexes containing lower concentrations of LPS were able to induce the transcription of IL-8. At 6 hr, the complex with 100 ng/ml of LPS increased the density ratio by 24 fold (P<0.05) when compared to LPS alone (FIG. 13). At 24 hr, complexes with LPS at 1, 10, 100, 1000 ng/ml increased the density ratio by 11, 16.8, 41, 6, and 12.5 fold, respectively, when compared to LPS alone at the same concentrations (P<0.05, FIG. 14). Thus, by 24 hr, LPS–rbosCD14 complex containing as low a concentration as 1 ng/ml of LPS was able to induce the transcription of IL-8, demonstrating that rbosCD14 sensitizes bovine mammary ductal epithelial cells to respond to LPS in vitro.

Example 9

Effect of rbosCD14 on Milk Somatic Cell Counts in Mammary Glands Injected with Low Concentration of LPS The concentration of sCD14 in milk and its correlation with Milk Somatic Cell Counts (MSCC) had not been previously determined because of the lack of a reliable ELISA for measuring bovine sCD14. The in vivo effects of a recombinant bovine soluble CD14 polypeptide, the rbosCD14 of the invention, were demonstrated by injecting LPS or LPS+rbosCD14 into mammary glands and measuring changes in MSSC. Quarter foremilk samples were taken aseptically 12 hr and immediately before the morning milking. Right and left rear quarters received 2 ml of LPS (*E. coli* 0111:B4, 1 µg/ml) and 2 ml of LPS preincubated with rbosCD14 (75 µg/ml) immediately after milking, respectively. The right and left front quarters received 2 ml of 0.8% NaCl and rbosCD14 (75 µg/ml in 0.8% NaCl), respectively. At 12, 24, 36, 48, 60, and 72 hr post injection, quarter milk samples were collected immediately before milking for the determination of total MSCC using a Foss electronic cell counter (Foss Food Technology, Eden Prairie, Minn.).

Figure 15:
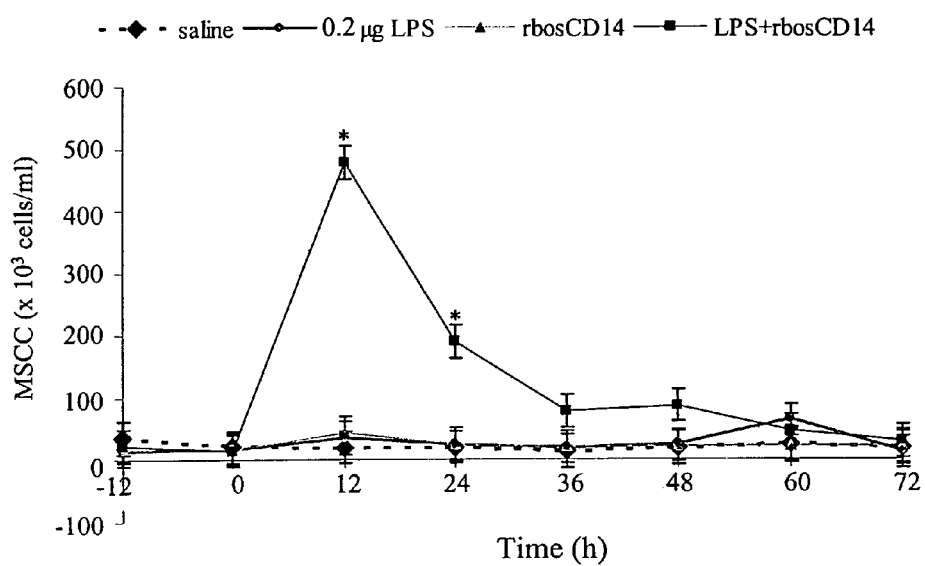
FIG. 15 depicts changes in milk somatic cell counts (MSCC) after intramammary injection. Each of the four mammary glands per cow was injected with saline, LPS (0.2 μg), rbosCD14 (75 μg), or LPS (0.2 μg)+rbosCD14 (75 μg) at 0 hr. Quarter milk samples were collected at −12, 0, 12, 24, 36, 48, 60, and 72 hr. The values are the means (±SE) of two cows. * denotes that means within the treatment groups differ ($P<0.05$).

Intramammary injection of 0.1 µg of LPS did not induce an increase in MSCC (P>0.05, FIG. 15). However, intramammary injection of LPS–rbosCD14 complex containing low concentrations of LPS resulted in an increase in MSCC at 12 and 24 hr after injection, indicating that rbosCD14 sensitizes bovine mammary ductal epithelial cells to respond to LPS in vivo (P<0.05, FIG. 15). Mammary glands injected with 0.9% NaCl or rbosCD14 alone did not show an increase in MSCC during the experimental period (P>0.05, FIG. 15).

Variation in the sensitivity of cows to LPS was observed during the present study. We reported results from cows that did not have an increase in MSCC after injection of 0.05 µg of LPS. Mammary glands of 4 out of 9 cows had an increase in MSCC after infusion with 0.1 µg of LPS. Similar to results reported in this study, two cows who did not respond to 0.1 µg of LPS had an increase in MSCC after injection of LPS–rbosCD14 complex containing 0.1 µg of LPS (data not shown). Variation in the kinetics of the MSCC increase after LPS or *E. coli* injection was also reported by others (Erskine et al., supra).

Example 10

Effect of Intramammary Injection of Recombinant Bovine Soluble CD14 (rbosCD14) in Cows Injected with *E. coli*.

Six lactating dairy cows free from intramammary infection were selected for study. On the day of experimental intramammary infection with *E. coli*, milk samples were collected before challenge (0 hour). After machine milking in the milking parlor, one mammary quarter was injected with 100 µl of rbosCD14 in 10 ml of physiological saline and one quarter with 10 ml of physiological saline. Both quarters were immediately challenged with 50 colony forming units (CFU) of *E. coli* suspended in 1 ml of physiological saline. Milk samples were collected from 4 cows at 6, 12, 16, 20, 24, 48, and 72 hours after challenge and from 2 cows at 4, 8, 12, 16, 20, 24, 48, and 72 hours after challenge. The milk samples were assayed for presence of *E. coli* and for milk somatic cells (white blood cells, a measure of mammary gland inflammation). Clinical symptoms such as body temperature, udder swelling, and abnormal milk were also determined at the same time points.

All mammary quarters injected with rbosCD14 either did not become infected or had the infection cleared by 24 hours after challenge with *E. coli*, e.g., cow 1816. All quarters injected with saline became infected and large numbers of bacteria were detected within 12 hours after challenge (Table 2). Counts for 5 cows injected with saline remained high for 48 to 72 hours after infection. The infection for one cow (1861) was cleared from the gland by 20 hours after challenge.

Somatic cell counts for mammary quarters injected with rbosCD14 increased sooner when compared to cows injected with saline (Table 2). This was attributed to the binding of LPS produced by the *E. coli* to rbosCD14 and the binding of the LPS/rboCD14 complex to epithelial cells. This binding initiated recruitment of somatic cells into the challenged quarters and elimination of the *E. coli*.

Saline injected quarters were swollen and hard 12 hours after challenge. Milk from those quarters contained numerous clumps and was yellow in color. The rbosCD14 quarters remained normal when compared to the two uninjected quarters. Thus, intrammammary injection of rbosCD14 prevented infection by *E. coli*.

TABLE 2

Somatic cell counts and bacteriology for mammary quarters injected with either saline or rbosCD14 and challenged with 50 cfu of *E. coli*.

| #1274 | | 0 h | 6 h | 12 h | 24 h | 48 h | | | |
|---|---|---|---|---|---|---|---|---|---|
| *E. coli* + saline | SCC (1000/ml) | 280 | 255 | 1749.5 | 5554 | 2533 | | | |
| | Bacteriology (cfu/ml) | N/A | 13300 | 12600 | 10500 | | | | |
| *E. coli* + 100 ug sCD14 | SCC (1000/ml) | 242 | 667 | 10020 | 16378 | 4787.5 | | | |
| | Bacteriology (cfu/ml) | N/A | 900 | 100 | 0 | | | | |

| #1678 | | 0 h | 6 h | 12 h | 24 h | 48 h | 72 h | | |
|---|---|---|---|---|---|---|---|---|---|
| *E. coli* + saline | SCC (1000/ml) | 298 | 493.5 | 599 | 20054.5 | 1976.5 | 9704.5 | | |
| | Bacteriology (cfu/ml) | N/A | 0 | 1000 | 900 | 700 | 100 | | |
| *E. coli* + 100 ug sCD14 | SCC (1000/ml) | 242 | 3833 | 4684.5 | 4491 | 2032.5 | 1095 | | |
| | Bacteriology (cfu/ml) | N/A | 0 | 0 | 0 | 0 | 0 | | |

| #1816 | | 0 h | 4 h | 8 h | 12 h | 16 h | 20 h | 24 h | 48 h | 72 h |
|---|---|---|---|---|---|---|---|---|---|---|
| *E. coli* + saline | SCC (1000/ml) | 187 | 485 | 429 | 244.5 | 221 | 7275.5 | 37425.5 | 7758 | 3197 |
| | Bacteriology (cfu/ml) | N/A | 25 | 175 | 2125 | >25000 | 250 | 75 | 100 | 0 |
| *E. coli* + 100 ug sCD14 | SCC (1000/ml) | 119.5 | 280.5 | 470.5 | 703 | 683 | 1947.5 | 4002 | 9705.5 | 9123.5 |
| | Bacteriology (cfu/ml) | N/A | 0 | 50 | 175 | 400 | 250 | 0 | 0 | 0 |

| #1850 | | 0 h | 4 h | 8 h | 12 h | 16 h | 20 h | 24 h | 48 h | 72 h |
|---|---|---|---|---|---|---|---|---|---|---|
| *E. coli* + saline | SCC (1000/ml) | 306.5 | 376.5 | 395.5 | 209 | 9063.5 | 41948.5 | 62884 | 63341 | 15797.5 |
| | Bacteriology (cfu/ml) | N/A | 0 | 6250 | NC | 3400 | 775 | 575 | 175 | 0 |
| *E. coli* + 100 ug sCD14 | SCC (1000/ml) | 376 | 297 | 401 | 428 | 15726 | 66101.5 | 68362 | 51784.5 | 19627.5 |
| | Bacteriology (cfu/ml) | N/A | 0 | 1125 | 12500 | 1000 | 125 | 25 | 0 | 0 |

| #1861 | | 0 h | 6 h | 12 h | 16 h | 20 h | 24 h | 48 h | 72 h | |
|---|---|---|---|---|---|---|---|---|---|---|
| *E. coli* + saline | SCC (1000/ml) | 437.5 | 626 | 253 | 4412 | 51030 | 53641 | 16405 | 12208 | |
| | Bacteriology (cfu/ml) | N/A | 50 | 500 | 50 | 0 | 0 | 0 | 0 | |
| *E. coli* + 100 ug sCD14 | SCC (1000/ml) | 166 | 11580.5 | 17273.5 | 11874 | 5915.5 | 5402 | 3757.5 | 4218.5 | |
| | Bacteriology (cfu/ml) | N/A | 0 | 0 | 0 | 0 | 0 | 0 | 0 | |

| #2044 | | 0 h | 6 h | 12 h | 16 h | 20 h | 24 h | 48 h | 72 h | |
|---|---|---|---|---|---|---|---|---|---|---|
| *E. coli* + saline | SCC (1000/ml) | 285.5 | 215.5 | 21083.5 | 53028 | 68783.5 | 88017 | 11612.5 | 2977.5 | |
| | Bacteriology (cfu/ml) | N/A | 1875 | 1975 | 150 | 125 | 0 | 0 | 0 | |
| *E. coli* + 100 ug sCD14 | SCC (1000/ml) | 102.5 | 14466.5 | 7343.5 | 1795.5 | 913 | 764 | 1500.5 | 510 | |
| | Bacteriology (cfu/ml) | N/A | 0 | 0 | 0 | 0 | 0 | 0 | 0 | |

Example 11

Effect of Intraperitoneal Injection of a Recombinant Bovine Soluble CD14 (rbosCD14) on Survival of Mice Injected With Endotoxin Eighty-one female mice were randomly assigned into two groups and injected intraperitoneally (IP) with either endotoxin (8 µg/g of body weight, n=41) or endotoxin plus rbosCD14 (6.8 µg/g of body weight, n=40). The survival rate of the injected mice was monitored every 12 hours for 60 hours.

Figure 16:
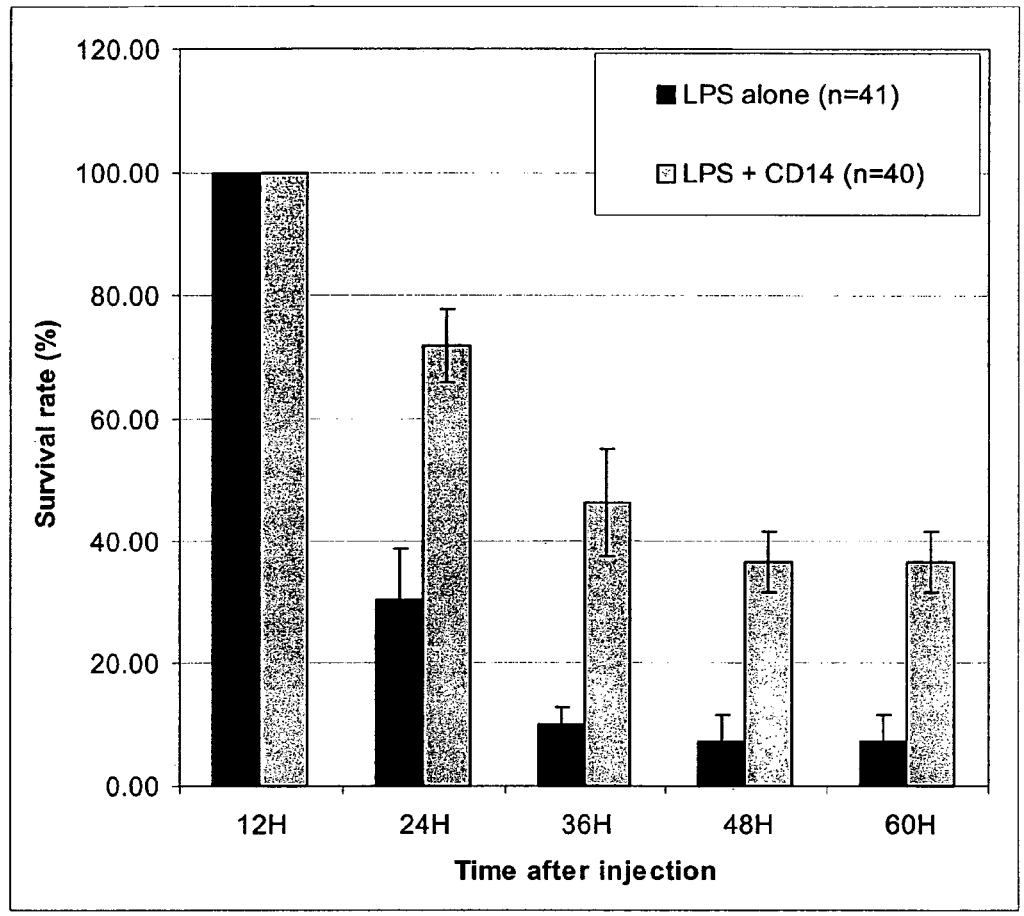
FIG. 16 depicts the survival rate in mice injected with either LPS or LPS plus rbosCD14.

Survival rate for mice injected with LPS at 24 hours averaged 30% compared to 70% for mice injected with LPS and rbosCD14. Survival rate for rbosCD14-LPS injected mice remained higher than for mice receiving LPS without rbosCD14 and averaged 38 and 4%, respectively, at 60 hours after injection (FIG. 16). Thus, the rbosCD14 reduced mortality in mice injected with LPS.

For statistical analysis, data from all experiments, supra, were analyzed using the GLM procedure of SAS (SAS Institute Inc., Cary, N.C.). Data are expressed as the mean ±SE.

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

We claim:

1. A method for sensitizing bovine mammary cells to respond to LPS comprising:
   (a) administering an isolated recombinant bovine soluble CD14 polypeptide, rbosCD14, consisting of the amino acid sequence of SEQ ID NO:2, wherein the amino acid in position 343 of SEQ ID NO:2 is valine or isoleucine, to a subject in need thereof; and
   (b) determining that said cells have been sensitized by observing increased milk somatic cell counts (MSCC) or transcription of IL-8 in response to a concentration of LPS lower than that known to induce said increased MSCC or transcription in the absence of rbosCD14.

* * * * *